US008809521B2

(12) United States Patent (10) Patent No.: US 8,809,521 B2
Melvik et al. (45) Date of Patent: Aug. 19, 2014

(54) DELAYED SELF-GELLING ALGINATE SYSTEMS AND USES THEREOF

(75) Inventors: Jan Egil Melvik, Oslo (NO); Jorunn E. Bjornstad, Tranby (NO); Terje Svendsen, Asker (NO)

(73) Assignee: FMC Biopolymer AS, Sandvika (NO)

( * ) Notice: Subject to any disclaimer, the term of this patent is extended or adjusted under 35 U.S.C. 154(b) by 208 days.

(21) Appl. No.: 12/675,166

(22) PCT Filed: Aug. 28, 2008

(86) PCT No.: PCT/US2008/010193
§ 371 (c)(1),
(2), (4) Date: Feb. 25, 2010

(87) PCT Pub. No.: WO2009/032158
PCT Pub. Date: Mar. 12, 2009

(65) Prior Publication Data
US 2011/0053886 A1 Mar. 3, 2011

Related U.S. Application Data

(60) Provisional application No. 60/966,437, filed on Aug. 28, 2007.

(51) Int. Cl.
*C07H 3/00* (2006.01)
*C08B 37/00* (2006.01)
*C12P 19/04* (2006.01)
*A01N 43/04* (2006.01)
*A61K 31/715* (2006.01)

(52) U.S. Cl.
USPC ............................................ 536/123; 514/54

(58) Field of Classification Search
None
See application file for complete search history.

(56) References Cited

U.S. PATENT DOCUMENTS

| | | |
|---|---|---|
| 1,814,981 A | 7/1931 | Thornley et al. |
| 2,420,308 A | 5/1947 | Gates et al. |
| 4,789,734 A | 12/1988 | Pierschbacher et al. |
| 4,792,525 A | 12/1988 | Ruoslahti et al. |
| 4,879,237 A | 11/1989 | Ruoslahti et al. |
| 4,988,621 A | 1/1991 | Ruoslahti et al. |
| 5,175,093 A | 12/1992 | Seifert |
| 5,266,326 A | 11/1993 | Barry et al. |
| 5,531,716 A | 7/1996 | Luzio et al. |
| 5,965,997 A | 10/1999 | Alwardi et al. |
| 6,090,763 A | 7/2000 | Stewart et al. |
| 6,121,441 A | 9/2000 | Simensen et al. |
| 6,129,761 A | 10/2000 | Hubbel |
| 6,136,334 A | 10/2000 | Viegas et al. |
| 6,146,655 A | 11/2000 | Ruben |
| 6,150,581 A | 11/2000 | Jiang et al. |
| 6,309,380 B1 | 10/2001 | Larson et al. |
| 6,407,226 B1 | 6/2002 | Simensen et al. |
| 6,432,449 B1 | 8/2002 | Goldenberg et al. |
| 6,497,902 B1 | 12/2002 | Ma |
| 6,534,083 B2 | 3/2003 | Gilding et al. |
| 6,592,566 B2 | 7/2003 | Kipke et al. |
| 6,629,947 B1 | 10/2003 | Sahatjian et al. |
| 6,638,917 B1 | 10/2003 | Li et al. |
| 6,642,363 B1 | 11/2003 | Mooney et al. |
| 6,656,508 B2 | 12/2003 | Goldenberg et al. |
| 6,656,974 B1 | 12/2003 | Renn et al. |
| 6,730,298 B2 | 5/2004 | Griffith-Cima et al. |
| 6,793,675 B2 | 9/2004 | Shapiro et al. |
| 7,790,699 B2 | 9/2010 | Melvik et al. |
| 2001/0055588 A1 | 12/2001 | Griffith-Cima et al. |
| 2003/0044391 A1 | 3/2003 | Elliott et al. |
| 2004/0037812 A1 | 2/2004 | Giannetti et al. |
| 2005/0169895 A1 | 8/2005 | Melvik et al. |
| 2006/0159823 A1 | 7/2006 | Melvik et al. |
| 2007/0054043 A1 | 3/2007 | Gaserod et al. |

FOREIGN PATENT DOCUMENTS

| | | |
|---|---|---|
| EP | 0 345 886 A | 12/1989 |
| GB | 666 961 A | 2/1952 |
| GB | 1 399 822 A | 7/1975 |
| JP | 5208917 | 8/1993 |
| WO | WO 94/10976 | 5/1994 |
| WO | WO 94/25080 | 11/1994 |
| WO | WO 99/15211 | 4/1999 |
| WO | WO 00/09566 | 2/2000 |
| WO | WO 01/05370 | 1/2001 |
| WO | WO 03/041758 | 5/2003 |
| WO | WO 2004011628 A1 | 2/2004 |
| WO | WO 2004/032904 | 4/2004 |

OTHER PUBLICATIONS

Skaugrud O. et al. "Biomedical and Pharmaceutical Applications of Alginate and Chitosan", Biotechnology and Genetic Engineering Reviews vol. 16: p. 23-40, Apr. 1999.

Andrews, R. T., et al, "Relative rates of blood reduction during transcatheter arterial embolization with tris-acryl gelatin microspheres or polyvinyl alcohol; quantitative comparison in a swine model," *J. Vasc Interv Radio* 14, 1311-1316 (2003).

Arica, B., et al, "5-Flourouracil encapsulated alginate beads for the treatment of breast cancer," *Int J Pharm* 242, 267, (2002).

Aspden, T.J., et al, "Chitosan as a nasal delivery system: evaluation of the effect of chiosan mucociliary clearance rate in the frog palate model," *Int. J Pharm* 122, 69-78, (1995).

(Continued)

*Primary Examiner* — Layla Bland

(74) *Attorney, Agent, or Firm* — FMC Corporation

(57) ABSTRACT

Dispersions that comprise insoluble alginate/gelling ion particles in an alginate solution, wherein the dispersion exhibits less than 10% of final gel storage modulus after one minute in the absence of addition of non-gelling cations are disclosed. Kits and compositions for making such dispersions are disclosed and methods for making and using the dispersions, and the components used in the dispersions are also disclosed.

40 Claims, 4 Drawing Sheets

(56) References Cited

OTHER PUBLICATIONS

Atala, A., et al, "Endoscopic treatment of vesicoureteral reflux with a chondrocyte-alignate suspension," *Journal of Urology* 152, 641-643(1994).

Atala, A., et al, "Injectable alginate seeded with chondrocytes as a potential treatment for vesicoureteral reflux," *Journal of Urology* 150, 745-747 (1993).

Becker, T.A., et al, "Flow properties of liquid calcium alginate polymer injected through medical microcatheters for endovascular embolization," *Journal of Biomedical Materials Research*, 61, 533-540 (2002).

Becker, T.A., et al, "Calcium alginate gel: a biocompatible and mechanically stable polymer for endovascular embolization," *Journal of Biomedical Materials Research* 54, 76-86 (2001).

Becker, T.A., et al, "In vivo assessment of calcium alginate gel for endovascular embolization of a cerebral arteriovenous malformation model using the Swine rete mirabile," *Neurosurgery* 51, 453-459 (2002).

Brunetti, P, et al, "Immunoprotection of pancreatic islet grafts within artificial microcapsules," *Int J Artific Org* 14, 789-791 (1991).

Caldamone, A.A., et al, "Long-term results of the endoscopic correction of vesicoureteral reflux in children using autologous chondrocytes," *Journal of Urology* 165, 2224-2227 (2001).

Caterson, E. J., et al, "Polymer/alginate amalgam for cartilage-tissue engineering," *Ann NY Acad Sci*, 961, 134-128 (2002).

Chang, S.C., et al, "Injection molding of chondrocyte/alignate constructs in the shape of facial implants," *Journal of Biomedical Materials Research* 55, 503-511 (2001).

Clark, A.H., et al, "Structural and mechanical properties of biopolymer gels," *Advances in Polymer Science* 83, 57-192 (1987).

Cohen, S.B., et al., "The use of absorbable co-polymer pads with alginate and cells for articular cartilage repair in rabbits," *Biomaterials* 24, 2653-2660 (2003).

de Blok, S., et al, "Fatal sepsis after uterine artery embolization with microspheres," *J Vasc Interv Radiol* 14, 779-783 (2003).

Diamond, D.A., et al, "Mechanisms of failure of endoscopic treatment of vesicoureteral reflux based on endoscopic anatomy," *Journal of Urology* 170,1556-1559 (2003).

Diamond, D.A., et al, "Endoscopic correction of vesicoureteral refulx in children using autologous chondrocytes: preliminary results," *Journal of Urology* 162, 1185-1188 (1999).

Diduch, David R., "Marrow Stromal Cells Embedded in Alginate for repair of Osteochondral Defects," *Arthrocscopy:The Journal of Arthroscopic and Related Surgery*, (2000), vol. 16, No. 6, 571-577.

Domm, C, et al, "Redifferentiation of dedifferentiated bovine articular chondrocytes in alginate culture under low oxygen tension," *Osteoarthritis and Cartilage* 10, 13-22 (2002).

Dornish, J.M., et al, "Standards and guidelines for biopolymers in tissue-engineered medical products. ASTM alginate and chitosan standard guides," *Ann N Y Acad Sci* 944, 388-397 (2001).

Draget, K.J., "Homogeneous Alginate Gels: A Technical Approach," *Carbohydrate Polymers*, 14, 159-178, (1991).

Draget, K.I., et al, "Ionic and acid gel formation of epimerised alginates: The effect of AlgE4," *Int J Biol Macromol* 27, 117-122 (2000).

Frangonas, E. et al., "Articular cartilage repair in rabbits by using suspensions of allogenic chondrocytes in alginate," *Biomaterials* 21, 795-801 (2000).

Grant, G.T., et al, "Biological interactions between polysa ccharides and divalent cations: The egg-box model," *FEBS Lett* 32, 195, 198 (1973).

Gutowska, A., et al, "Injectable gels for tissue engineering," *Anatomical record* 263, 342-349 (2001).

Hart, A. McKay, et al, "Exogenous leukaemia inhibitory factor enhances nerve regeneration after late secondary repair using a bioartificial nerve conduit," *British Journal of Plastic Surgeons* 56, 444-450 (2003).

Hashimoto, T., et al, "Peripheral nerve regeneration through alginate gel: analysis of early outgrowth and late increase in diameter of regenerating axons," *Exp Brain Res* 146, 356-368 (2002).

Homicz, M.R., et al.,"Human septal chondrocyte redifferentiation in alginate, polyglycolic acid scaffold, and monolayer culture," *Laryngoscope* 113, 25-32 (2003).

Kataoka, K., et al, "Alginate, a bioresorbable material derived from brown seaweed, enhances elongation of amputated axons of spinal cord in infant rats," *J. Biomed Mater Res* 54, 373-384 (2001).

Kavalkovich, K.V., et al, "Chondrogenic differentiation of human mesenchymal stem cells within an alginate layer of culture system," *In Vitro Cell Dev Biol* 38, 457-466 (2002).

Kim, M.D., et al, "Uterine artery embolization for adenomyosis without fibroids," *Clin Radiol* 59, 520-526 (2004).

Knight, M.M, et al, "Cell and nucleus deformation in compressed chondrocyte-alignate constructs: temporal changes and calculation of cell modulus," *Biochim Biophys Acta* 1570, 1-8 (2002).

Kuo, C.K., et al, "Ionically crosslinked alginate hydrogels as scaffolds for tissue engineering: part 1. Structure, gelation rate and mechanical properties," *Biomaterials* 22, 511-521 (2001).

Lansdown, A.B.G., "Calcium: a potential central regulator in wound healing in the skin," *Wound Repair Regen* 10, 271-285 (2002).

Lanza, R. P., et al, "Xenotransplantation of porcine and bovine islets without immunosuppression using uncoated alginate microspheres," *Transplantation* 59, 1377-1384 (1995).

Lee, D.A., et al, "Expansion of chondrocytes for tissue engineering in alginate beads enhances chondrocytic phenotype compared to conventional monolayer techniques," *Acta Orthop Scand* 74, 6-15 (2003).

Li, S., et al, "Studies on alginate-chitosan microcapsules and renal arterial embolization in rabbits," *J Contolled Release* 84, 87-98 (2002).

Ma, P.X, "Scaffolds for tissue fabrication," *Materials Today* 7, 30-40 (2004).

Mandel, K.G., et al, "Review article: Alginate-raft formulations in the treatment of heartburn and acid reflux," *Aliment Pharmacol Ther* 14, 669-690 (2000).

Mandl, E. W., et al, "Fibroblast growth factor-2 in serum-free medium is a potent mitogen and reduces dedifferentiation of human ear chondrocytes in monolayer culture," *Matrix Biol* 23, 231-241 (2004).

Mandl, E. W., et al, "Serum-Free Medium Supplemented with High-concentration FGF2 for Cell Expansion Culture of Human Ear Chondrocytes Promotes Redifferentiation Capacity," *Tissue Eng* 8, 573-580 (2002).

Melvik, J.E., et al, "Alginate as a carrier for cell immobilization." *Fundamentals of Cell Immobilisation Biotechnology* vol. 8A. (Ed V. Nedovic and R. Willaert) Kluwer, (2004).

Melvik J.E. et al., "Key characterization parameters of alginate for use in biomedical and pharmaceutical applications," Pronova Biomedical, presented at Bioencapsulation VII, Easton, USA, (1998).

Mierisch, C.M., et al. "Chondrocyte transplantation into articular cartilage defects with use of calcium alginate: the fate of the cells," *J Bone Joint Surg Am* 85-A, 1757-1767 (2003).

Miralles, G., et al, "Sodium alginate sponges with or without sodium hyaluronate; In vitro engineering of cartilage," *Journal of Biomedical Materials Research* 57, 268-278 (2001).

Mosahebi, A., et al, "A novel use of alginate hydrogel as Schwann Cell matrix." *Tissue Engineering* 7, 525-534 (2001).

Orive, et al, "Cell encapsulation: promise and progress," *Nature Medicine* 9, No. 1, 104-407 (2003).

Paige, K.T., et al, "De novo cartilage generation using calcium alginate-chondrocyte constructs," *Plast Reconstr Surg* 97, 179-180 (1996).

Paige, K.T., et al, "Injectable cartilage," *Plast Reconstr Surg* 96, 1390-1398 (1995).

Risberg, B, "Adhesions: preventive strategies," *Eur J Surg Suppl* 577, 32-29 (1997).

Rowley, J.A., et al, "Alignate type and RGD density control myoblast phenotype," *Journal of Biomedical Materials Research* 60, 217-223 (2002).

(56) References Cited

OTHER PUBLICATIONS

Safley, S.A., et al, "Proliferative and cytokine responses in CTLA4-Ig-treated diabetic NOD mice transplanted with microencapsulated neonatal porcine ICCs," *Cell Transplant* 11, 695-705 (2002).
Shapiro, L, et al, "Novel Alginate sponges for cell culture and transplantation," *Biomaterials* 18, 583-590 (1997).
Siskin, G. P., et al, "Pathologic Evaluation of a Spherical Polyvinyl Alcohol Embolic Agent in a Porcine Renal Model," *J Vasc Interv Radiol* 14, 89-98 (2003).
Skjåk-Braek, G., et al, "Application of alginate gels in biotechnology and biomedicine," *Carbohydrates in Europe* 14, 19-25 (1996).
Stevens, M. M., et, al "A rapid-curing alginate gel system: utility in periosteum-derived cartilage tissue engineering," *Biomaterials* 25, 887-894 (2004).
Storrs, R., et al, "Preclinical development of the Islet Sheet," *Ann N Y Acad Sci* 944, 252-266 (2001).
Sufan, W., et al, "Sciatic nerve regeneration through alginate with tabulation or nontubulation repair in cat," *Journal of Neurotrauma* 18, 329-338 (2001).
Sutherland, I.W., "Alginates. In Biomaterials; Novel materials from biological sources," (Ed. D. Byrom) pp. 309-331, New York 1991.
Thomas S., "Alginate dressing in surgery and wound management—Part 1," *Journal of Wound Care*, vol. 9, No. 2, (2000), p. 56-60.
Thomas S., "Alginate dressing in surgery and wound management—Part 2," *Journal of Wound Care*, vol. 9, No. 3, (2000), p. 115-119.
Thomas S., "Alginate dressing in surgery and wound management—Part 3," *Journal of Wound Care*, vol. 9, No. 4, (2000), p. 163-166.
Tonnesen, H.H., et al, "Alginate in drug delivery systems," *Drug Development and Industrial Pharmacy* 28, 621-630 (2002).
Tse, M., et al, "Secretion of recombinant proteins from hydroxymethyl methacrylate-methyl methacrylate capsules," *Biotechnoogy and Bioengineering* 51, 271-280 (1996).
Wang, L., et al, "Evaluation of sodium alginate for bone marrow cell tissue engineering," *Biomaterials* 24, 3475-3481 (2003).
Westhaus, E., et al, "Triggered release of calcium from lipid vesicles: a bioinspired strategy for repaid gelation of polysaccharide and protein hydrogels," *Biomaterials* 22, 453-462 (2001).
Geng et al. "Alginate and its Physical and Chemical Properties When Used as a Biomacromolecule Carrier", Jiangsu Pharmacy and Clinic Research, 2002, (10)2, p. 61-63.
Winn S.R. et al., "Polymer-encapsulated Cells Genetically Modified to Secrete Human Nerve Growth Factor Promote the Survival of Axotomized Septal Cholinergic Neurons," Proc. Natl. Acad. Sci. USA 91, 2324-2328 (1994).
Yoon, W., "Embolic Agents Used for Bronchial Artery Embolisation in massive haemoptysis", Expert Opin. Pharmacother 5, p. 361-367 (2004).

DELAYED SELF-GELLING ALGINATE SYSTEMS AND USES THEREOF

This application claims priority to U.S. Provisional Application Ser. No. 60/966,437; filed Aug. 28, 2007, which is incorporated herein by reference.

FIELD OF THE INVENTION

The present invention relates to alginate systems which have a delayed gelling process and to compositions, devices, kits and methods of making and using such systems.

BACKGROUND OF THE INVENTION

Alginates are hydrophilic marine biopolymers with the unique ability to form heat-stable gels that can develop and set at physiologically relevant temperatures.

Alginates are a family of non-branched binary copolymers of 1-4 glycosidically linked β-D-mannuronic acid (M) and α-L-guluronic acid (G) residues. The relative amount of the two uronic acid monomers and their sequential arrangement along the polymer chain vary widely, depending on the origin of the alginate. Alginate is the structural polymer in marine brown algae such as *Laminaria hyperborea, Macrocystis pyrifera, Lessonia nigrescens* and *Ascophyllum nodosum*. Alginate is also produced by certain bacteria such as *Pseudomonas aeruginosa, Azotobacter vinelandii* and *Pseudomonas fluorescens* (WO04011628 A1).

Alginate gels are produced when a divalent cation forms ionic bonds with the negatively charged group from a G residue from each of two different alginate polymers, thereby cross-linking the two polymers. The formation of multiple cross-linkages among numerous alginate polymers results in the matrix that is the alginate gel structure.

Alginate gels can be hydrogels, i.e. cross-linked alginate polymers that contain large amounts of water without dissolution. Biopolymer gels, such as alginate hydrogels are attractive candidates for tissue engineering and other biomedical applications. Because of this and the ability to form gels under physiologic conditions, alginates are widely used and studied for encapsulation purposes and as a biostructure material. The entrapment of cells in alginate beads is a commonly used technique. Also alginates have been shown to be useful material for other types of biostructures, including tissue engineering applications and as scaffolds for nerve regenerations.

Different methods for making alginate hydrogels exist. The most common method is the dialysis/diffusion method where the alginate solution is gelled by diffusion of gelling ions from an outer reservoir. This method is mostly used when making alginate gel beads and in food applications. The manufacturing of alginate microbeads is a rapid process limited by the diffusion of gelling ions into the gel network. Although this process is well suitable for entrapment of cells in microbeads, it is less useful for the production of other shapes or structures. For manufacturing of gel structures of larger size diffusion gelling systems may have limited possibility. This is because the rapid gelling process limits the time to allow shaping of the gel structure.

A delay in the gelling process may be used to allow for the injection of solutions into the body and/or to mix cells or other biomaterial into the gel matrix prior to the gel forming. Therefore, alternative methods have been developed for the manufacturing of other types of biocompatible alginate gel structures. The gelling speed may be reduced by using internal gelling systems of which the gelling ions are released more slowly inside the forming gel. This is described as internal setting of the gel. Commonly, in an internal gelling system, a calcium salt with limited solubility, or complexed $Ca^{2+}$ ions, are mixed with an alginate solution into which the calcium ions are slowly released. Calcium sulfate has been used in alginate based cell delivery vehicles for tissue engineering. The release of calcium and gelling kinetics may also be controlled by using calcium salts with pH dependent solubility and the addition of a slowly acting acid such as D-glucono-δ-lactone (GDL). As the pH changes, calcium ions are released. Also calcium containing liposomes have been used as a controllable alginate gelling system. Alginate gel systems based upon internal gelling may have a more defined and limited supply of gelling ions as opposed to diffusion systems where calcium ions are allowed to diffuse into the alginate solution to give a calcium saturated gel.

Various current methods for manufacturing of alginate gel structures have limitations. Some techniques are only useful to make gels of limited sizes and shapes. Depending of the applications there may problems associated with the control of the gelling kinetics. In some case, undesirable materials are present in gels because such materials are residues and by-products of chemically controlled gelling mechanisms. In some cases, non-physiologic pH values are required for gelling and such conditions may present limitations to the use of such methods. There is therefore a need for other gelling systems and formulations.

SUMMARY OF THE INVENTION

The present invention relates to dispersions that comprise insoluble alginate/gelling ion particles in an alginate solution, wherein the dispersion exhibits less than 10% of final gel storage modulus after one minute in the absence of addition of non-gelling cations.

The present invention further relates to kits for producing an alginate gel. The kits comprise a first container comprising soluble alginate, and a second container comprising insoluble alginate/gelling ion particles.

The present invention further relates to compositions for preparing alginate gels. The compositions comprise immediately soluble alginate and insoluble alginate/gelling ion particles.

The present invention further relates to methods for dispensing delayed self-gelling alginate dispersion. The methods comprise forming a dispersion of insoluble alginate/gelling ion particles in a solution of soluble alginate, and dispensing the dispersion whereby the dispersion forms an alginate gel matrix.

The present invention further relates to methods for dispensing delayed self-gelling alginate dispersion into an individual. The methods comprise forming a dispersion of insoluble alginate/gelling ion particles in a solution of soluble alginate, and dispensing the dispersion into an individual whereby the dispersion forms an alginate gel matrix in the individual.

The present invention further relates to methods for dispensing delayed self-gelling alginate dispersion into an individual for use as tissue bulking material, for use in a vascular embolization procedure, for use to prevent post surgical adhesion formation, for use in wound treatment procedures, for use in diabetes treatments and for use in treatment of arthritis.

The present invention further relates to methods of using an implantable alginate gel. The methods comprise forming delayed self gelling alginate by dispensing delayed self gelling alginate dispersion and, following gel formation, implanting the implantable alginate gel into an individual.

The present invention further relates to methods of producing implantable devices.

The present invention further relates to implantable devices comprising a homogenous alginate gel coating and methods of coating the same.

The present invention further relates to methods filling or repairing osteochondral defects resulting from osteoarthritis by dispensing a delayed self gelling alginate dispersion that includes chondrocytes into an individual's body or by implanting a biocompatible matrix that includes chondrocytes into an individual's body The present invention further relates to methods of treating diabetes by dispensing a delayed self gelling alginate dispersion that includes insulin-producing cells or multicellular aggregates into an individual's body or by implanting a biocompatible matrix that includes insulin-producing cells or multicellular aggregates into an individual's body.

The present invention further relates to methods of improving the viability of pancreatic islets, or other cellular aggregates or tissue, following isolation and during storage and transport by incorporating the islets, or cellular aggregates or tissue into a delayed self gelling alginate dispersion.

The present invention further relates to insoluble alginate/gelling ion particles and methods of producing the same.

DETAILED DESCRIPTION OF PREFERRED EMBODIMENTS

Figure 1:
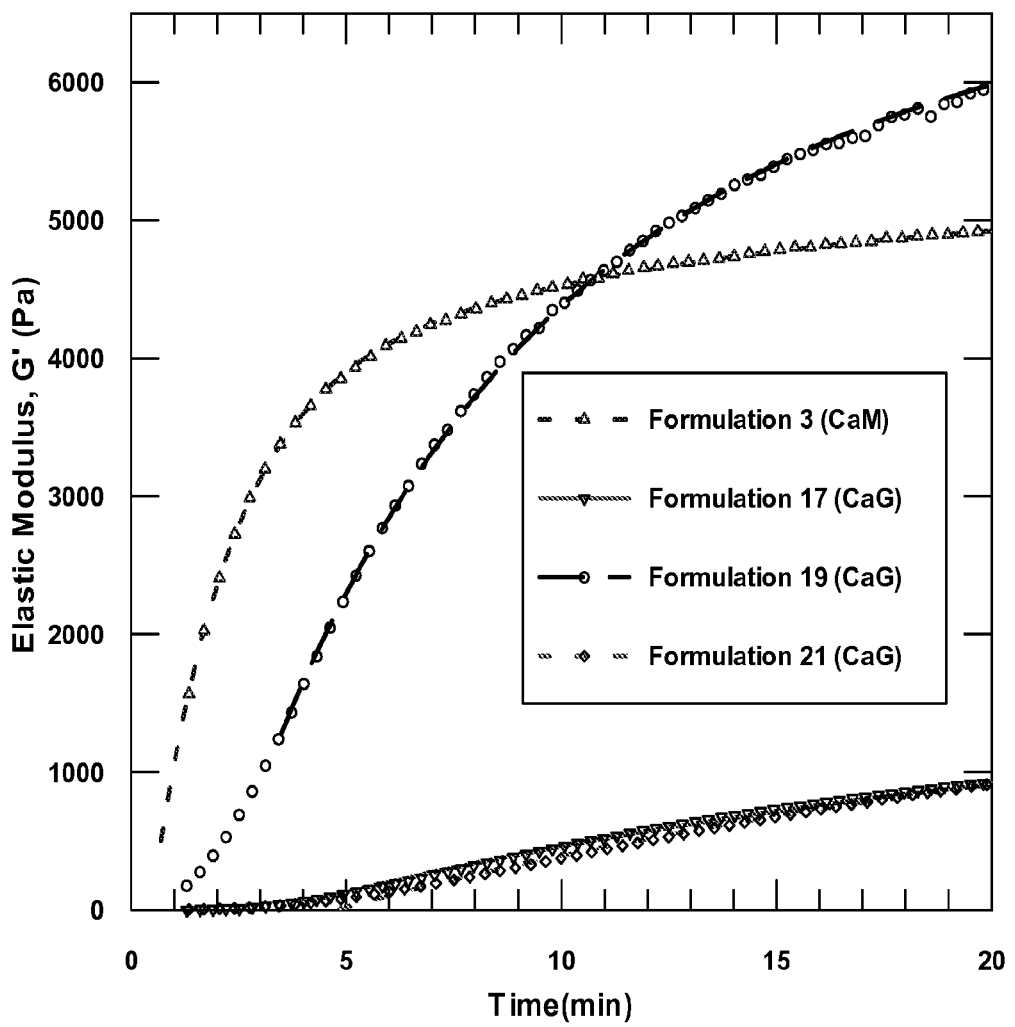
FIG. 1 shows the development of gel structure in Formulation 3, 17 and 19. In the figure, Time=zero at the start of mixing the two components.

Alternative alginate gelling systems, referred to as a "delayed self-gelling systems," are provided. These systems may be used in numerous biomedical applications as well as other applications, particularly if a delay in gelling is desired or required for periods of time so that the material may be delivered prior to a high degree of gelling. The systems may include alginate and gelling ions that have a high degree of biocompatibility. The system may provide for delays in gelling time which can be maintained for substantial lengths of time. Moreover, the system may provide for the ability to initiate or accelerate gelling by addition of non-gelling cations from another source.

The delayed self-gelling alginate technology provides increased control of the gelling properties of formulations, particularly control in the onset of gelation. The alginate systems of the present invention are useful in biomedical procedures and for inclusion in biomedical devices as well as in other biocompatible applications requiring precise control of gelling properties, particularly a time delay in the onset of gelling and/or control of the half-time for completion of gelling, and/or the time for completion of gelling. The improved control of the onset, duration, and completion gelling process may be used to optimize compositions and properties for applications requiring precise control including but not limited to biomedical applications including in vivo and in vitro medical devices. Examples of medical applications may include, but are not limited to: providing drug or peptide delivery devices; dispensing of cells, proteins, multicellular aggregates or detectable labels for tissue engineering; and coating, deposition or repair of defects in tissues or organs. Examples of implantable devices that may be used with or formed by these compositions include: device coating, cardiac pacemakers, catheters, implantable protheses, tissue bulking implants, esophageal reflux inhibiting implants, renal reflux inhibiting implants, incontinence inhibiting implants, breast implants, chin implants, a cheek implants, dental implants, pectoral implants, and formed alginate matrix implants such as a solid device or microcapsule with or without encapsulated cells.

Systems comprise two components: a soluble alginate; and insoluble alginate/gelling ion particles. When the components are combined in the presence of a solvent to form a dispersion of insoluble alginate/gelling ion particles in an alginate solution, the formation of alginate gel is significantly delayed such that the dispersion exhibits 10% or less of the storage modulus of the final gel after one minute or more. In some embodiments, the dispersion exhibits 10% or less of the storage modulus of the final gel in the absence of additional non-gelling cation after significantly longer periods of time, such as for example, two minutes, three minutes, four minutes, five minutes, six minutes, seven minutes, eight minutes, nine minutes, ten minutes, fifteen minutes, twenty minutes, thirty minutes, forty minutes, forty five minutes, sixty minutes, ninety minutes, one hundred twenty minutes, one hundred eighty minutes, two hundred forty minutes, three hundred minutes, or more. The gelling ions of the particles may not dissociate from the insoluble particles in sufficient amounts to produce a gel of 10% or less of the storage modulus of the final gel within these various times. The delay in gel formation to 10% or less of the storage modulus of the final gel provides the user with significant time to manipulate and work with the dispersion before the gel forms. The delay makes the system particularly useful in applications in which faster gelling times increase the difficulty in use of the material.

As used herein, the symbol "/" as used in the term "insoluble alginate/gelling ion particles" is meant to indicate that the particles referred to therein comprise both alginate molecules and gelling ions.

As used herein, the term "storage modulus" is used interchangeably with the terms "G'", "elasticity" and "elastic modulus". One skilled in the art can readily measure storage modulus by well known methodology. As used herein, the term "final gel" in the reference made herein to "the storage modulus of the final gel" is meant to refer a gel that forms to the point in which there is no further increase the storage modulus over time, the gel being formed from a dispersion of insoluble alginate/gelling ion particles in an alginate solution at 20° C. upon addition of a sodium chloride salt in an amount sufficient to raise the final concentration of sodium ions in the solution by 17 mM or more, or to reach a final concentration of 0.9% whichever is greater.

In some embodiments, the rate of gel formation may be accelerated upon addition of non-gelling cations to the dispersion. This addition provides non-gelling cations which may displace gelling ions from the insoluble particles and thereby increase their availability in the dispersion to form crosslinking bonds that include alginate polymers from the soluble alginate in the dispersion.

The initiation and control of gelation for delayed self gelling formulations is strongly dependent on the type of alginate used in the insoluble particles in the formulation. In particular, the degree to which the gelling ion may be dissociated from the insoluble alginate/gelling ion particles so as to be able to form cross linking bonds with alginate of the alginate solution has a direct effect on the delay time for the onset of delayed self-gelling alginate formulations. Delayed self-gelling may be achieved when the insoluble alginate/gelling ion particles used to prepare the dispersion are prepared from short oligomeric G blocks, or from alginate with a relatively high G-content ("high G alginate") of 50% or more. Further, delayed self-gelling may be achieved when the insoluble alginate/gelling ion particles used to prepare the dispersion are produced in processes which have slow stirred/mixing speeds in the preparation of starting materials, or when such insoluble alginate/gelling ion particles are produced in processes which use non-aqueous polar solvents in the preparation of starting materials. The rate by which the gelling cation becomes available as a free ion in the dispersion controls the rate of gelation. Thus, the degree to which an insoluble alginate/gelling ion particle retains gelling ion in the presence of non-gelling ion, or exchanges gelling ion in the presence of non-gelling ion, determines the rate of gelation of the dispersion.

The soluble alginate and insoluble alginate/gelling ion particles of the system may in some embodiments be mixed by stirring or by using a suitable mixing device. The gelling kinetics of the formulation may be further controlled by adjusting the relative concentration of the soluble alginate in solution to the concentration of the insoluble alginate particles in the dispersion; the relative content of gelling ion to alginate; the presence of non-gelling ions or other carbohydrates, temperature, the size of insoluble alginate/gelling ion particles, the content of cells, multicellular aggregates, tissues or other biomaterials to be entrapped in the gel or present during gelling, (the presence of impurities) and the types of alginates used, as well as the manufacturing process for the insoluble alginate particles and post manufacturing treatment of alginate starting materials. This alginate system may therefore be widely adapted to each particular application. For entrapment of cells, multicellular aggregates, tissues or other biomaterials within the forming gel, the solvent, the alginate solution or dispersion may be premixed with the material to be entrapped.

The dispersion may be dispensed within an individual as a liquid/slurry to a site where an alginate gel matrix is desirable. After the soluble alginate and insoluble alginate/gelling ion particles are mixed in the presence of a solvent; the dispersion is dispensed within an individual where it comes in contact with physiological conditions, including the presence of non-gelling ions. The gelation of the dispersion progresses and the alginate gel sets in situ.

As used herein, the term "delayed self-gelling" is meant to refer to the gelling process which occurs in a very limited manner when the soluble alginate and insoluble alginate/gelling ion particles are mixed in the presence of a solvent. A "delayed self gelling alginate" is an alginate dispersion or gel which includes or is formed by soluble alginate and insoluble alginate/gelling ion particles in a solvent that exhibits 10% or less of the storage modulus of the final gel after more than a minute of longer in the absence of additional non-gelling cation. In some delayed self gelling alginates, the dispersion exhibits 10% or less of the storage modulus of the final gel in the absence of additional non-gelling cation after significantly longer periods of time, such as for example, two minutes, three minutes, four minutes, five minutes, six minutes, seven minutes, eight minutes, nine minutes, ten minutes, fifteen minutes, twenty minutes, thirty minutes, forty minutes, forty five minutes, sixty minutes, ninety minutes, one hundred twenty minutes, one hundred eighty minutes, two hundred forty minutes, three hundred minutes, or more.

The components used in the system may be maintained prior to use in any of several forms. For example, the soluble alginate may be maintained in solution or as a powder. In some embodiments, the soluble alginate may be maintained as a powder that is immediately soluble such as when it is freeze dried. Similarly, the insoluble alginate/gelling ion particles may be maintained as a dispersion or as a powder.

Kits and compositions are provided which comprise components and ingredients for preparing dispersions with the properties as set forth herein. Moreover, insoluble alginate/gelling ion particles which are useful to prepare such dispersions are provided as are methods of using the dispersions and making gels formed from such dispersion. These methods may be adapted in several medical and manufacturing methods and gels and devices coated with gels made form the delayed self gelling technology are also provided.

In some embodiments, the dispersion that comprises the insoluble alginate/gelling ion particles in an aqueous solution comprising the soluble alginate exhibits less than 10% of final gel storage modulus after two minutes in the absence of addition of non-gelling cations. In some embodiments, the dispersion exhibits less than 10% of final gel storage modulus after three minutes in the absence of addition of non-gelling cations. In some embodiments, the dispersion exhibits less than 10% of final gel storage modulus after four minutes in the absence of addition of non-gelling cations. In some embodiments, the dispersion exhibits less than 10% of final gel storage modulus after five minutes in the absence of addition of non-gelling cations. In some embodiments, the dispersion exhibits less than 10% of final gel storage modulus after ten minutes in the absence of addition of non-gelling cations. In some embodiments, the dispersion exhibits less than 10% of final gel storage modulus after fifteen minutes in the absence of addition of non-gelling cations. In some embodiments, the dispersion exhibits less than 10% of final gel storage modulus after twenty minutes in the absence of addition of non-gelling cations. In some embodiments, the dispersion exhibits less than 10% of final gel storage modulus after thirty minutes in the absence of addition of non-gelling cations. In some embodiments, the dispersion exhibits less than 10% of final gel storage modulus after forty five minutes in the absence of addition of non-gelling cations. In some embodiments, the dispersion exhibits less than 10% of final gel storage modulus after sixty minutes or more in the absence of addition of non-gelling cations.

In some embodiments, the dispersion exhibits delayed self gelling as set forth above but will, upon addition of non-gelling cations, exhibit greater than 10% of final gel storage modulus one minute or more after addition of non-gelling cation. In some embodiments, the dispersion exhibits greater than 10% of final gel storage modulus two minute or more after addition of non-gelling cation. In some embodiments, the dispersion exhibits greater than 10% of final gel storage modulus two minutes or more after addition of non-gelling cation. In some embodiments, the dispersion greater than exhibits greater than 10% of final gel storage modulus three minutes or more after addition of non-gelling cation. In some embodiments, the dispersion exhibits greater than 10% of final gel storage modulus four minutes or more after addition of non-gelling cation. In some embodiments, the dispersion exhibits greater than 10% of final gel storage modulus five minutes or more after addition of non-gelling cation. In some embodiments, the dispersion exhibits greater than 10% of final gel storage modulus ten minutes or more after addition of non-gelling cation. In some embodiments, the dispersion exhibits greater than 10% of final gel storage modulus fifteen minutes or more after addition of non-gelling cation. In some embodiments, the dispersion exhibits greater than 10% of final gel storage modulus twenty minutes or more after addition of non-gelling cation. In some embodiments, the dispersion exhibits greater than 10% of final gel storage modulus thirty minutes or more after addition of non-gelling cation. In some embodiments, the dispersion exhibits greater than 10% of final gel storage modulus forty five minutes or more after addition of non-gelling cation. In some embodiments, the dispersion exhibits greater than 10% of final gel storage modulus sixty minutes or more after addition of non-gelling cation. In some embodiments, the dispersion exhibits greater than 10% of final gel storage modulus ninety minutes or more after addition of non-gelling cation. In some embodiments, the dispersion exhibits greater than 10% of final gel storage modulus one hundred twenty minutes or more after addition of non-gelling cation. In some embodiments, the dispersion exhibits greater than 10% of final gel storage modulus three hours or more after addition of non-gelling cation. In some embodiments, the dispersion exhibits greater than 10% of final gel storage modulus four hours or more after addition of non-gelling cation. In some embodiments, the dispersion exhibits greater than 10% of final gel storage modulus five hours or more after addition of non-gelling cation. In some embodiments, the dispersion exhibits greater than 10% of final gel storage modulus six hours or more after addition of non-gelling cation.

In some embodiments, the dispersion exhibits greater than 20% or more of final gel storage modulus within such time limits after addition of non-gelling cation as set forth in describing the various embodiments above. In some embodiments, the dispersion exhibits greater than 30% of final gel storage modulus within such time limits after addition of non-gelling cation as set forth in describing the various embodiments above. In some embodiments, the dispersion exhibits greater than 40% or more of final gel storage modulus within such time limits after addition of non-gelling cation as set forth in describing the various embodiments above. In some embodiments, the dispersion exhibits greater than 50% of final gel storage modulus within such time limits after addition of non-gelling cation as set forth in describing the various embodiments above. In some embodiments, the dispersion exhibits greater than 60% or more of final gel storage modulus within such time limits after addition of non-gelling cation as set forth in describing the various embodiments above. In some embodiments, the dispersion exhibits greater than 70% of final gel storage modulus within such time limits after addition of non-gelling cation as set forth in describing the various embodiments above. In some embodiments, the dispersion exhibits greater than 80% or more of final gel storage modulus within such time limits after addition of non-gelling cation as set forth in describing the various embodiments above. In some embodiments, the dispersion exhibits greater than 90% of final gel storage modulus within such time limits after addition of non-gelling cation as set forth in describing the various embodiments above. In some embodiments, the dispersion exhibits greater than 95% or more of final gel storage modulus within such time limits after addition of non-gelling cation as set forth in describing the various embodiments above. In some embodiments, the dispersion exhibits greater than 99% of final gel storage modulus within such time limits after addition of non-gelling cation as set forth in describing the various embodiments above.

As used herein, "addition of non-gelling cation" is meant to refer to the addition of non-gelling ion at a concentration sufficient to raise the overall concentration of the non-gelling ion of the dispersion by at least 0.01% or more. In some embodiments, the addition of non-gelling cation raises concentration sufficient to raise the overall concentration of the non-gelling ion of the dispersion by at least 0.05%, at least 0.1%, at least 0.2%, at least 0.3%, at least 0.4%, at least 0.5%, at least 0.6%, at least 0.7%, at least 0.8%, at least 0.9%, at least 1.0%, or more. Examples of non-gelling cations which may be added to accelerate gelling of a delayed self gel dispersion include $Na^+$, $Li^+$, $K^+$, $Fe^+$ and/or $H^+$ (i.e. various acids). In some embodiments, the added non-gelling cation is provided as an addition which is added to and mixed into the dispersion from a solution. In some embodiments, the added non-gelling cation is provided by the amount of non-gelling cation provided when the dispersion is dispersed into a physiologic space.

In some embodiments, the alginate polymers or combinations thereof used in the soluble alginate may be the same or different from those in the insoluble alginate/gelling ion particles.

The concentration of alginate, both soluble alginate and the alginate in the form of insoluble alginate/gelling ion particles in a dispersion relative to the amount of solvent affects gelling time, porosity, stability and biodegradability, gel strength and elasticity of gels and gels having specific properties may be prepared by using specific ratios of soluble alginate and insoluble alginate/gelling ion particles to solvent. Generally, the lower the concentration of alginate (for a given ratio of soluble alginate to insoluble alginate), the more biodegradable a gel will be. In some embodiments, approximately 0.5%, 0.75%, 1%, 1.25%, 1.5%, 2%, 2.5%, 3%, 4%, 5%, 6%, 7%, 8%, 9%, 10% or more alginate (soluble alginate and alginate in the form of insoluble alginate/gelling ion particles) may be used.

The relative concentration of the soluble alginate to alginate in the form of insoluble alginate/gelling ion particles in the dispersion affects gelling time, pore size, gel strength and elasticity of gels as well as stability and biodegradability and gels having specific properties may be prepared by using specific ratios of soluble alginate to insoluble alginate/gelling ion particles. In some embodiments, the concentration of soluble alginate is approximately equal to concentration of alginate in the form of insoluble alginate/gelling ion particles (1:1). In some embodiments, the concentration of alginate in the form of insoluble alginate/gelling ion particles is twice that of soluble alginate (2:1). In some embodiments, the concentration of alginate in the form of insoluble alginate/gelling ion particles is half that of soluble alginate (1:2). In some embodiments, the concentration of alginate in the form of insoluble alginate/gelling ion particles to soluble alginate is 1 to 0.7 (1:0.7). Generally, the less gelling ion present, the more biodegradable a gel will be. Reducing the concentration of insoluble alginate/gelling ion in the system may be used to create gels with lower stability and higher biodegradability as the gel network is less saturated with cross-linking ions. Delayed self gelling allows for the preparation of gels with lower concentrations of gelling ion to produce gels particularly well suited for biodegradable uses. In some preferred embodiments, alginate ratios of insoluble alginate/gelling ion particles to soluble alginate are: 5:1, 4:1, 3:1, 2:1, 1:1, 1:2, 1:3, 1:4 or 1:5.

The relative content of G and M monomers in the alginate polymers affects pore size, stability and biodegradability, gel strength and elasticity of gels. Alginate polymers contains large variations in the total content of M and G, and the relative content of sequence structures also varies largely (G-blocks, M-blocks and MG alternating sequences) as well as the length of the sequences along the polymer chain. Generally, the lower the G content relative to M content in the alginate polymers used the more biodegradable a gel will be. Gels with high G content alginate generally have larger pore sizes and stronger gel strength relative to gels with high M alginate, which have smaller pore sizes and lower gel strength. In some embodiments, one or more of the alginate polymers of the alginate matrix contain more than 50% α-L-guluronic acid. In some embodiments, one or more of the alginate polymers of the alginate matrix contain more than 60% α-L-guluronic acid. In some embodiments, one or more of the alginate polymers of the alginate matrix contain 60% to 80% α-L-guluronic acid. In some embodiments, one or more of the alginate polymers of the alginate matrix contain 65% to 75% α-L-guluronic acid. In some embodiments, one or more of the alginate polymers of the alginate matrix contain more than 70% α-L-guluronic acid. In some embodiments, one or more of the alginate polymers of the alginate matrix does not contain 70% α-L-guluronic acid, nor 60% α-L-guluronic acid, nor 50% α-L-guluronic acid or less, nor 60% to 80% α-L-guluronic acid nor 65% to 75% α-L-guluronic acid. In some embodiments, one or more of the alginate polymers of the alginate matrix does not contain 70% α-L-guluronic acid, nor 60% α-L-guluronic acid, nor 50% α-L-guluronic acid or less, nor 60% to 80% α-L-guluronic acid nor 65% to 75% α-L-guluronic acid wherein the average MW of the alginate is between 2-20 kDa, in some embodiments between 2-10 kDa, in some embodiments between 2-5 kDa in some embodiments between 3-5 kDa and wherein in some such embodiments, the alginate polymer contains 10-25 monomers, or mostly oligomers having 15-19 monomers, or oligomers having an average of 16-18 monomers. In some embodiments, one or more of the alginate polymers of the alginate matrix contain at least more than 85% α-L-guluronic acid. In some embodiments, one or more of the alginate polymers of the alginate matrix contain at least more than 88% α-L-guluronic acid. In some embodiments, one or more of the alginate polymers of the alginate matrix contain at least more than 89% α-L-guluronic acid. In some embodiments, one or more of the alginate polymers of the alginate matrix contain at least more than 90% α-L-guluronic acid. In some embodiments, one or more of the alginate polymers of the alginate matrix contain at least more than 91% α-L-guluronic acid. In some embodiments, one or more of the alginate polymers of the alginate matrix contain at least more than 92% α-L-guluronic acid. In some embodiments, one or more of the alginate polymers of the alginate matrix contain at least more than 93% α-L-guluronic acid. In some embodiments, one or more of the alginate polymers of the alginate matrix contain at least more than 94% α-L-guluronic acid. In some embodiments, one or more of the alginate polymers of the alginate matrix contain at least more than 95% α-L-guluronic acid. In some embodiments, one or more of the alginate polymers of the alginate matrix contain at least more than 96% α-L-guluronic acid. In some embodiments, one or more of the alginate polymers of the alginate matrix contain at least more than 97% α-L-guluronic acid. In some embodiments, one or more of the alginate polymers of the alginate matrix contain at least more than 98% α-L-guluronic acid. In some embodiments, one or more of the alginate polymers of the alginate matrix contain at least more than 85% α-L-guluronic acid to at least more than 99% α-L-guluronic acid may have a molecular weight of between 2-20 kDa, in some embodiments between 2-10 kDa, in some embodiments between 2-5 kDa in some embodiments between 3-5 kDa. In some such embodiments, the alginate polymer contains 10-25 monomers. In some such embodiments, the alginate polymer contains mostly oligomers having 15-19 monomers. In some such embodiments, the alginate polymer contains oligomers having an average of 16-18 monomers. In some embodiments, one or more of the alginate polymers of the alginate matrix contain more than 50% C-5 epimer β-D-mannuronic acid. In some embodiments, one or more of the alginate polymers of the alginate matrix contain more than 60% C-5 epimer β-D-mannuronic acid. In some embodiments, one or more of the alginate polymers of the alginate matrix contain 60% to 80% C-5 epimer β-D-mannuronic acid. In some embodiments, one or more of the alginate polymers of the alginate matrix contain 65% to 75% C-5 epimer β-D-mannuronic acid. In some embodiments, one or more of the alginate polymers of the alginate matrix contain more than 70% C-5 epimer β-D-mannuronic acid. Procedures for producing uronic blocks from are disclosed in U.S. Pat. No. 6,121,441, which is incorporated herein by reference. G-block alginate polymers and their uses as modulators of alginate gel properties are set forth in U.S. Pat. No. 6,407,226, which is incorporated herein by reference. Some preferred embodiments, 30% G, 35% G, 40% G, 45% G, 50% G, 55% G, 60% G, 65% G, 70% G, 75%, 80% G or 85% G. Some preferred embodiments, are greater than 85% G.

The average molecular weight of alginate polymers affects gelling time, pore size, gel strength and elasticity of gels. Alginate polymers may have average molecular weights ranging from 2 to 1000 kD. The molecular weight of alginates may affect gel formation and the final gel properties. Generally, the lower the molecular weight of the alginate used the more biodegradable a gel will be. The alginate polymers or combinations thereof used in the soluble alginate components may be the same or different from the polymers or combinations thereof used in the insoluble alginate/gelling ion particles. In some embodiments, the alginate polymers of the alginate matrix have an average molecule weight of from 5 to 350 kD. In some embodiments, the alginate polymers of the alginate matrix have an average molecule weight of from 2 to 100 kD. In some embodiments, the alginate polymers of the alginate matrix have an average molecule weight of from 50 to 500 kD. In some embodiments, the alginate polymers of the alginate matrix have an average molecule weight of from 100 to 1000 kD. In some embodiments, the alginate polymers of the alginate matrix have an average molecule weight of from 2 to 50 kD. In some embodiments, the alginate polymers of the alginate matrix have an average molecule weight of from 2 to 40 kD. In some embodiments, the alginate polymers of the alginate matrix have an average molecule weight of from 2 to 30 kD. In some embodiments, the alginate polymers of the alginate matrix have an average molecule weight of from 2 to 20 kD. In some embodiments, the alginate polymers of the alginate matrix have an average molecule weight of from 2 to 15 kD. In some embodiments, the alginate polymers of the alginate matrix have an average molecule weight of from 2 to 10 kD. In some embodiments, the alginate polymers of the alginate matrix have an average molecule weight of from 2 to 5 kD. In some embodiments, the alginate polymers of the alginate matrix have an average molecule weight of from 3 to 15 kD. In some embodiments, the alginate polymers of the alginate matrix have an average molecule weight of from 3 to 10 kD. In some embodiments, the alginate polymers of the alginate matrix have an average molecule weight of from 3 to 5 kD. In some embodiments, the average number of monomers of an alginate oligomer is 15-20, 16-19, 17-18, 5, 6, 7, 8, 9, 10, 11, 12, 13, 14, 15, 16, 17, 18, 19, 20, 21 or 22.

In some embodiments, gels are designed to have a high degree of biodegradability. Accordingly, gels having less alginate, less gelling ion lower G content and lower molecular weight alginates can be produced using the lower limits of one or more of these parameters as set forth herein to produce gels with a high degree of biodegradability.

The alginate may possess a viscosity in a 1% solution measured at 20 degrees centigrade of from 25 to 1000 mPas and in some embodiments, preferentially 50 to 1000 mPas (1% solution, 20 C).

In some embodiments, the alginate is sterile. In some embodiments, the alginate is sterile ultrapure alginate. In some embodiments, the sterile alginate is produced using sterility filters.

The alginate that may be used herein is desirably ultrapure when such are to be used for medical implantation applications; e.g., having endotoxin content below 400 eu/g, in some embodiments below 300 eu/g, in some embodiments below 200 eu/g, in some embodiments below 100 eu/g, in some embodiments below 75 eu/g, and in some embodiments below 50 eu/g. In some embodiments, the alginate has an endotoxin level of <25 EU/gram.

In some embodiments, it is preferred that methods of manufacture of insoluble alginate/gelling ion particles provide products with stoichiometric amount (100% saturation) of gelling ion. Use of such stoichiometric salts imparts greater reproducibility in the delayed self-gelling alginate systems. In some embodiments, it is preferred that method of manufacture of insoluble alginate/gelling ion particles provide products with sub-stoichiometric amount (<100% saturation) of said gelling ion. Use of such sub-stoichiometric salts imparts biodegradability to delayed self-gelling alginate systems.

In some embodiments, the alginate used to prepare the insoluble alginate/gelling ion particles is G block oligomers having about 60% or more, 70% or more, 80% or more, 85% or more, 90% or more, 95% or more, 99% G content. The MW of G-block alginates are generally below 10 kDa which corresponds to average DPn of 57 units and typically have a MW at around 3 kDa which corresponds to a DPn of a 17.

In some embodiments, the insoluble alginate/gelling ion particles are particles of standard high G alginates and, in some embodiments, Ca, which gives a few minutes delay. In some embodiments, these alginates have a MW typically between 50 kDa (286 units) and 350 kDa (2000 units).

In some embodiments, the insoluble alginate/gelling ion particles are particles of standard high M alginates or MG alginates.

G block alginate oligomers refers to isolated fractions of oligomers containing an average of about 17 G monomers per oligomer, the majority of which are 15-19 monomers per oligomer. These fractions may be produced by processing naturally occurring high G alginates and separating the G block alginate by various means such as fractionation.

In some embodiments, the alginate is ultrapure alginate. Ultrapure alginate is commercially available such as from different sources of seaweed like *Laminaria Hyperborea*. Commercial calcium salts of alginic acid are generally manufactured in processes whereby calcium is added to alginic acid in the solid phase by simple admixture and kneading of the components together. Examples of commercially available calcium salts of alginic acid are Protaweld (from FMC BioPolymer) and Kelset from ISP Corporation.

In some embodiments, the insoluble alginate/gelling ion particles may be produced using alginate and/or G block oligomers by making an alginate gel using the alginate and/or G block oligomers and a gelling ion, washing out sodium or other ions that were present in the alginate and/or G block oligomers, drying the gel to remove the water, and making particles from the dried gel. In some embodiments, the insoluble alginate/gelling ion particles made using alginate and/or G block oligomers are stoichiometric salts. Insoluble alginate/gelling ion particles made using alginate and/or G block oligomers preferably have a high purity and a specific, consistent and generally uniform content of gelling ion such as, for example, calcium or strontium, barium, zinc, iron, manganese, copper, lead, cobalt, nickel, or combinations thereof, such that gel formation speed and gel strength can be provided with more precise predictability. Insoluble alkaline earth salts of alginic acid such as for example calcium alginate or strontium alginate (depending upon the gelling ion used) or insoluble transition metal salts of alginic acid (such as those using gelling ions of copper, nickel, zinc, lead, iron, manganese or cobalt) can be manufactured with a known and pre-determined content of alkaline earth ions by precipitation from the solutions. In some embodiments, a sodium alginate solution is prepared using alginate and/or G block oligomers. Optionally, sodium salt such as sodium carbonate may be included in the sodium alginate solution. A salt containing the desired gelling ion for the insoluble alginate/gelling ion particle, such as for example, calcium salt or strontium salt such as calcium chloride or strontium chloride, is used to make a solution. The sodium alginate solution is combined, preferably slowly, with the gelling ion solution. Preferably, the combined solutions are continuously stirred during the mixing process. Insoluble alginate particles, such as for example calcium alginate or strontium alginate (depending upon the gelling ion used), precipitate from the combined solutions. The precipitated insoluble alginate is then be removed from the solution and washed repeatedly, such as 2-10 times, with purified water for example to remove all soluble ions. The removal of soluble ions is confirmed for example by testing the conductivity of insoluble alginate in purified water compared to the conductivity of purified water. After washing, the insoluble alginate can be dried, such as with a vacuum. The dried alginate can be milled and, in some embodiments, selected for particle sizes.

In some embodiments, the insoluble alginate/gelling ion particles may be prepared using a non-aqueous solvent to produce an alginate solution from which a gel is formed and the particles are produced. The insoluble alginate/gelling ion particles may be produced using alginate by making an alginate gel using alginate, a gelling ion and a solvent other than water, washing out sodium or other ions from the gel that were present in the alginate, drying the gel to remove the solvent, and making particles from the dried gel. The dried alginate can be milled and, in some embodiments, selected for particle sizes. Examples of non-water solvents are polar solvent such as alcohols which include methanol, ethanol, propanol, isopropanol, butanol, etc. In some embodiments, the insoluble alginate/gelling ion particles are stoichiometric salts. Insoluble alginate/gelling ion particles preferably have a high purity and a specific, consistent and generally uniform content of gelling ion such as, for example, calcium or strontium barium, zinc, iron, manganese, copper, lead, cobalt, nickel, or combinations thereof, such that gel formation speed and gel strength can be provided with more precise predictability. Insoluble alkaline earth salts of alginic acid such as for example calcium alginate or strontium alginate (depending upon the gelling ion used) or insoluble transition metal salts of alginic acid (such as those using gelling ions of copper, nickel, zinc, lead, iron, manganese or cobalt) can be manufactured with a known and pre-determined content of alkaline earth ions by precipitation from the solutions. In some embodiments, commercially available sodium alginate is first used to prepare a sodium alginate solution using a non-water solvent. Examples of non-water solvents are polar solvent such as alcohols which include methanol, ethanol, propanol, isopropanol, butanol, etc. Optionally, sodium salt such as sodium carbonate may be included in the sodium alginate solution. A salt containing the desired gelling ion for the insoluble alginate/gelling ion particle, such as for example, calcium salt or strontium salt such as calcium chloride or strontium chloride, is used to make a solution. The sodium alginate non-water solution is combined, preferably slowly, with the gelling ion non-water solution. Preferably, the combined non-water solutions are continuously stirred during the mixing process. Insoluble alginate particles, such as for example calcium alginate or strontium alginate (depending upon the gelling ion used), precipitates from the combined solutions. The precipitated insoluble alginate is then be removed from the solution and washed repeatedly, such as 2-10 times, with purified water for example to remove all soluble ions. The removal of soluble ions is confirmed for example by testing the conductivity of insoluble alginate in purified water compared to the conductivity of purified water. After washing, the insoluble alginate can be dried, such as with a vacuum. The dried alginate can be milled and, in some embodiments, selected for particle sizes.

In some embodiments, the alginate matrix is may be coated with a polycationic polymer like a poly amino acid or chitosan after the gel matrix forms. In some embodiments, poly-lysine is the polycationic polymer. In some embodiments, poly-lysine is linked to another moiety and the poly-lysine is thus used to facilitate association of the moiety to the gel. Examples of moieties linked to the gel using polycationic polymers include, for example, drugs, peptides, contrast reagents, receptor binding ligands or other detectable labels. Some specific examples include vascular endothelial growth factor (VEGF), epidermal growth factor (EGF), transforming growth factor (TGF), and bone morphogenic protein (BMP). Drugs may include cancer chemotherapeutic agents such as Taxol, cis-platin and/or other platinum-containing derivatives. Carbohydrate polymers may include hyaluronan, chitosan, heparin, laminarin, fucoidan, chondroitin sulfate. In some embodiments, the alginates used are modified alginate polymers such as chemically modified alginate in which one or more polymers are linked to a different alginate polymer. Examples of such modified alginate polymers may be found in U.S. Pat. No. 6,642,363, which is incorporated herein by reference.

In some embodiments, the alginate polymer may include a non-alginate moiety such as, for example, a drug, a peptide, a contrast reagent, a receptor binding ligand or other detectable label. In one embodiment, the alginate polymer includes an RDG peptide (Arg-Asp-Gly), a radioactive moiety (e.g. $^{131}$I) or a radio opaque substance. Other examples of moieties linked to alginate polymers include, for example, drugs, peptides, contrast reagents, receptor binding ligands or other detectable labels. Some specific examples include vascular endothelial growth factor (VEGF), epidermal growth factor (EGF), transforming growth factor (TGF), and bone morphogenic protein (BMP). Drugs may include cancer chemotherapeutic agents such as Taxol, cis-platin and/or other platinum-containing derivatives. Carbohydrate polymers may include hyaluronan, chitosan, heparin, laminarin, fucoidan, chondroitin sulfate.

In some embodiments, the alginate may be covalently bound to at least one peptide comprising one or more cell adhesion sequences. For example, modified alginates are disclosed in U.S. Pat. No. 6,642,363 (Mooney), which is incorporated herein by reference. In some embodiments, peptide linked alginates are mixed with non-modified alginate. Peptide-coupled alginates may be used for example in immobilizing cells to promote cell proliferation and cell differentiation. Peptide-coupled alginates may also be employed in combination with other peptide-coupled polysaccharides and/or with non-modified polysaccharides.

U.S. Pat. Nos. 4,988,621, 4,792,525, 5,965,997, 4,879,237, 4,789,734 and 6,642,363, which are incorporated herein by reference, disclose numerous examples of cell adhesion sequence peptides. Suitable peptides include, but are not limited to, peptides having about 10 amino acids or less. In some embodiments, cell attachment peptides comprise RGD, YIGSR (SEQ ID NO:1), IKVAV (SEQ ID NO:2), REDV (SEQ ID NO:3), DGEA (SEQ ID NO:4), VGVAPG (SEQ ID NO:5), GRGDS (SEQ ID NO:6), LDV, RGDV (SEQ ID NO:7), PDSGR (SEQ ID NO:8), RYVVLPR (SEQ ID NO:9), LGTIPG (SEQ ID NO:10), LAG, RGDS (SEQ ID NO:11), RGDF (SEQ ID NO:12), HHLGGALQAGDV (SEQ ID NO:13), VTCG (SEQ ID NO:14), SDGD (SEQ ID NO:15), GREDVY (SEQ ID NO:16), GRGDY (SEQ ID NO:17), GRGDSP (SEQ ID NO:18), VAPG (SEQ ID NO:19), GGGGRGDSP (SEQ ID NO:20) and GGGGRGDY (SEQ ID NO:21) and FTLCFD (SEQ ID NO:22). In some embodiments, cell attachment peptides comprise RGD, YIGSR (SEQ ID NO:1), IKVAV (SEQ ID NO:2), REDV (SEQ ID NO:3), DGEA (SEQ ID NO:4), VGVAPG (SEQ ID NO:5), GRGDS (SEQ ID NO:6), LDV, RGDV (SEQ ID NO:7), PDSGR (SEQ ID NO:8), RYVVLPR (SEQ ID NO:9), LGTIPG (SEQ ID NO:10), LAG, RGDS (SEQ ID NO:11), RGDF (SEQ ID NO:12), HHLGGALQAGDV (SEQ ID NO:13), VTCG (SEQ ID NO:14), SDGD (SEQ ID NO:15), GREDVY (SEQ ID NO:16), GRGDY (SEQ ID NO:17), GRGDSP (SEQ ID NO:18), VAPG (SEQ ID NO:19), GGGGRGDSP (SEQ ID NO:20) and GGGGRGDY (SEQ ID NO:21) and FTLCFD (SEQ ID NO:22) and further comprise additional amino acids, such as for example, 1-10 additional amino acids, including but not limited 1-10 G residues at the N or C terminal. For example, a suitable peptide may have the formula $(Xaa)_n$-SEQ-$(Xaa)_n$ wherein Xaa are each independently any amino acid, n=0-7 and SEQ=a peptide sequence selected from the group consisting of: RGD, YIGSR (SEQ ID NO:1), IKVAV (SEQ ID NO:2), REDV (SEQ ID NO:3), DGEA (SEQ ID NO:4), VGVAPG (SEQ ID NO:5), GRGDS (SEQ ID NO:6), LDV, RGDV (SEQ ID NO:7), PDSGR (SEQ ID NO:8), RYVVLPR (SEQ ID NO:9), LGTIPG (SEQ ID NO:10), LAG, RGDS (SEQ ID NO:11), RGDF (SEQ ID NO:12), HHLGGALQAGDV (SEQ ID NO:13), VTCG (SEQ ID NO:14), SDGD (SEQ ID NO:15), GREDVY (SEQ ID NO:16), GRGDY (SEQ ID NO:17), GRGDSP (SEQ ID NO:18), VAPG (SEQ ID NO:19), GGGGRGDSP (SEQ ID NO:20) and GGGGRGDY (SEQ ID NO:21) and FTLCFD (SEQ ID NO:22), and the total number of amino acids is less than 22, preferably less that 20, preferably less that 18, preferably less that 16, preferably less that 14, preferably less that 12, preferably less that 10. In some embodiments, cell attachment peptides consist of RGD, YIGSR (SEQ ID NO:1), IKVAV (SEQ ID NO:2), REDV (SEQ ID NO:3), DGEA (SEQ ID NO:4), VGVAPG (SEQ ID NO:5), GRGDS (SEQ ID NO:6), LDV, RGDV (SEQ ID NO:7), PDSGR (SEQ ID NO:8), RYVVLPR (SEQ ID NO:9), LGTIPG (SEQ ID NO:10), LAG, RGDS (SEQ ID NO:11), RGDF (SEQ ID NO:12), HHLGGALQAGDV (SEQ ID NO:13), VTCG (SEQ ID NO:14), SDGD (SEQ ID NO:15), GREDVY (SEQ ID NO:16), GRGDY (SEQ ID NO:17), GRGDSP (SEQ ID NO:18), VAPG (SEQ ID NO:19), GGGGRGDSP (SEQ ID NO:20) and GGGGRGDY (SEQ ID NO:21) and FTLCFD (SEQ ID NO:22). Biologically active molecules for cell adhesion or other cellular interaction may include EGF, VEGF, b-FGF, FGF, TGF, TGF-β or proteoglycans. Cell attachment peptides comprising RGD may be in some embodiments, 3, 4, 5, 6, 7, 8, 9 or 10 amino acids in length. Examples include, but are not limited to, RGD, GRGDS (SEQ ID NO:6), RGDV (SEQ ID NO:7), RGDS (SEQ ID NO:11), RGDF (SEQ ID NO:12), GRGDY (SEQ ID NO:17), GRGDSP (SEQ ID NO:18), GGGGRGDSP (SEQ ID NO:20) and GGGGRGDY (SEQ ID NO:21). Suitable cell adhesion peptides comprising RGD include, but are not limited to NOVATACH RGD (NovaMatrix, FMC BioPolymer, Oslo, Norway) and those disclosed in U.S. Pat. No. 6,642,363, which is hereby incorporated by reference in its entirety. Peptide synthesis services are available from numerous companies, including Commonwealth Biotechnologies, Inc. of Richmond, Va., USA. Chemical techniques for coupling peptides to the alginate backbones may be found in U.S. Pat. No. 6,642,363.

As used herein, the term "an RGD modified alginate" refers to an alginate which is covalently linked to a peptide comprising RGD. Suitable RGD peptide coupled alginates include, but are not limited to, NOVATACH RGD (NovaMatrix, FMC BioPolymer, Oslo, Norway) and those disclosed in U.S. Pat. No. 6,642,363, which is hereby incorporated by reference in its entirety.

The soluble alginate may be a salt such as, for example, $Na^+$-alginate, $K^+$-alginate, PEG-alginate (polyethylene glycol-alginate), $NH_4$-alginate or combinations thereof.

In some embodiments, the soluble alginate is freeze dried or otherwise desiccated. Freeze dried soluble alginate is "immediately soluble." "Immediately soluble" alginate is soluble in water in less than one minute, preferably less than 30 seconds, more preferably less than 15 seconds. "Readily soluble" alginate takes more than one minute and usually several minutes to go into solution.

The gelling ions used in the insoluble alginate/gelling ion particles affects gelling kinetics, gel strength, and elasticity. Gelling ions also have affects on cell growth. The gelling ions used in the insoluble alginate/gelling ion particles may be $Ca^{++}$, $Sr^{++}$, $Ba^{++}$, $Zn^{++}$, $Fe^{++}$, $Mn^{++}$, $Cu^{++}$, Pb, Co, Ni, or combinations thereof.

The insoluble alginate gelling ion complexes are particles. The particles are generally non fibrous based on L/D ratio where the particle shape is characterized by a largest dimension (L) and smallest dimension (D). Non-fibrous L/D is less than 10, preferably less than 5, preferably less than 2. An L/D of 10 or more is a chopped fiber. The insoluble alginate gelling ion can be maintained as a dispersion or in dry form. If the former, the dispersion can be mixed with a solution containing soluble alginate or with immediately soluble alginate to form a dispersion of insoluble alginate/gelling ion particles in a solution containing soluble alginate. If the insoluble alginate gelling ion particles are in dry form, they may be mixed with dry immediately soluble alginate and subsequently with a solution to form a dispersion of insoluble alginate/gelling ion particles in a solution containing soluble alginate or the dry insoluble alginate gelling ion particles may be combined with a solution containing soluble alginate to form a dispersion of insoluble alginate gelling ion particles in a solution containing soluble alginate.

The agitation that occurs upon mixing the components to form the dispersion results in distribution of the solid particles within the solution. The dispersion so produced can be in the form of a slurry which can be poured, injected and otherwise delayed self gel within a mold or cavity to form the shape of such mold or cavity.

The dispersion of insoluble alginate gelling ion particles in a solution containing soluble alginate is formed, it is dispensed to the site where the delayed self gelling occurs to form an alginate gel. In some embodiments, the dispersion is dispensed to a site in vivo. In some embodiments, the dispersion is dispensed on to a site on an individual's body. In some embodiments, the dispersion is dispensed into a mold or other container or surface.

The concentration of gelling ions used in the insoluble alginate/gelling ion particles affects gelling kinetics, gel strength, and elasticity. The higher the concentration of gelling ions, the higher the gel strength. Gel strength is highest when the gel is saturated with gelling ion. Conversely, the lower the concentration of gelling ion, the lower the gel strength and higher the degree of biodegradability.

The particle size of the insoluble alginate/gelling ion particles may affects gelling kinetics and the final properties of the gel. The smaller the particle size the more rapid the completion of gel formation. Larger particle sizes produce stronger gels. Particle sizes may be controlled by, for example, sifting insoluble alginate/gelling ion particles through various different size filters such that the particles can be generally all be within a predetermined size range. In some embodiments, particles are <25 µm, 25-45 µm, 45-75 µm, 75-125 µm or >125 µm. In some embodiments, particles are <125 µm, <135 µm, <145 µm, <155 µm, <165 µm or <175 µm.

The solvent used may be, for example, water, saline, sugar solution, cell culture solution, a solution such as a drug solution, protein, or nucleic acid solution, a suspension such as a cell suspension, liposomes, or a contrast reagent suspension. The solvent must not contain sufficient available non-gelling cations to accelerate gelation in the absence of addition of non-gelling ion. That is, the solvent must not contain non-gelling cations which can initiate displacement of gelling cations from the insoluble alginate/gelling ion particles at a rate sufficient to result in gel formation to greater than 10% storage modulus of the final gel within a designated time as set forth herein. Thus, for example, any non-gelling cations in the solvent must be associated with a counter ion or other molecular entity such that the non-gelling cation, while present, is not available. The sodium in a solution of sodium alginate is not available to the extent that the number of sodium ions is equal to the number of negative ionic charges present in the alginate counter ion molecule. An increase in the number of available sodium ions by the addition of a salt, for example, such as sodium chloride, in which the sodium ion does not associate with the chlorine counterion to the same degree that the sodium ion associates with the alginate counterion in sodium alginate, can accelerate gelation due to the presence of the available non-gelling sodium cation if the presence is sufficient, i.e. if sufficient salt is added. The solvent that is used to prepare the soluble alginate solution used in the dispersion must contain insufficient amounts of non-gelling ion such that the gel formed by the dispersion does not have a storage modulus of greater than 10% the storage modulus of the final gel within a designated time absent addition of non-gelling ion.

The alginate hydrogel formed may comprise, for example, drugs nucleic acid molecules, cells, multicellular aggregates, tissue, proteins, enzymes, liposomes, a contrast reagent or a biologically active material. Examples of a biologically active material are hyaluronate and chitosan. Contrast reagents include tantalum and gadolinium. Some specific examples of proteins include vascular endothelial growth factor (VEGF), epidermal growth factor (EGF), transforming growth factor (TGF), and bone morphogenic protein (BMP). Drugs may include cancer chemotherapeutic agents such as Taxol, cis-platin and/or other platinum-containing derivatives. Carbohydrate polymers may include hyaluronan, chitosan, heparin, laminarin, fucoidan, chondroitin sulfate.

The cells that can be used in the gels include non-recombinant and recombinant cells. In some embodiments in which cells are encapsulated within an alginate matrix, encapsulated cells are mammalian cells, preferably human cells. In some embodiments in which encapsulated cells are non-proliferating cells, the non-proliferating cells may be selected from the group consisting of: pancreatic islets, hepatic cells, neural cells, renal cortex cells, vascular endothelial cells, thyroid and parathyroid cells, adrenal cells, thymic cells, ovarian cells and chondrocytes. In some embodiments in which encapsulated cells are proliferating cells, the proliferating cells may be stem cells, progenitor cells, proliferating cells of specific organs, fibroblasts and keratinocytes or cells derived from established cell lines, such as for example, 293, MDCK and C2C12 cell lines. In some embodiments, encapsulated cells comprise an expression vector that encodes one or more proteins that are expressed when the cells are maintained. In some embodiments, the protein is a cytokine, a growth factor, insulin or an angiogenesis inhibitor such as angiostatin or endostatin, other therapeutic proteins or other therapeutic molecules such as drugs. Proteins with a lower MW, less than about 60-70 kD, are particularly good candidates because of the porosity of the gel-network. In some embodiments, the cells are present as multicellular aggregates or tissue.

There are numerous applications for delayed self-gelling alginate. In some embodiments, the delayed self-gelling alginate is used in food products. The delayed self-gelling alginates are particularly useful in those food products which are prepared as a liquid/slurry mixture with other food ingredients and dispensed into a vessel. The vessel is preferably a mold where the gel/food product sets to form a solid or semi-solid with a molded shape. Candies, edible decorations, puddings and other molded shape food products can be prepared. Gelling may be initiated by addition of a non-gelling cation.

In some embodiments, the delayed self-gelling alginates are used in biomedical applications. Biocompatible delayed-gelling alginates may be applied topically. The biocompatible delayed self-gelling alginates are particularly useful in those biomedical applications in which it is desired for the gel matrix to conform to a space in situ such that the delayed self-gelling alginate can be dispensed as a dispersion into the site where the matrix is desired. The dispersion fills the cavity or space in liquid/slurry form and, upon interaction with physiological non-gelling cations sets to form a solid within the cavity or space. Alternatively, the dispersion may be dispensed topically where it can be spread prior to setting. In some embodiments, the delayed self-gelling alginates are used in the manufacture of matrices which can be prepared with specific shapes by preparing a liquid/slurry mixture that is dispensed into a mold where it sets to form a solid with a molded shape and/or to prepare matrices with encapsulated cells useful as tissue or organ replacements. Gelling may be initiated by addition of a non-gelling cation.

Alginate delayed self-gelling systems that are controllable, biocompatible and particularly designed for in situ gel formation implantation purposes are provided which have delayed self gelling properties that allow for ease of use and manipulation without time constraints associated with other systems. Solutions that can easily be used for injections or applied in other ways inside or outside the body are provided which set to form solid gel matrices, in some cases upon addition of non-gelling cation and/or by exposure to physiological non-gelling cations. By mixing a soluble alginate, a solvent and a gelling ion source of which the gelling ions are bound within the gel network of an insoluble particle, the gel forming material can be dispensed as a liquid and set in a desirable pattern and time frame. The solution at a predefined time hardens and forms a gel or the gelling may be accelerated with the addition or exposure to a source of non-gelling cations. The formulation is biocompatible, as variations in pH and presence of toxic compounds are omitted. Significant deviations from biologic pH are unnecessary.

In some embodiments, the delayed self gelling alginate is used in biomedical applications such as tissue bulking such as for the treatment of reflux problems (i.e. treatment of incontinence, renal reflux or esophageal reflux problems), embolization such as in the treatment of benign or malignant tumors, anti-adhesion treatment as post-surgical procedures, and wound treatment. The current technology may be used in several applications, including tissue constructs ex vivo or in vivo, as cells or other biomaterials may be mixed into the gelling system thereby creating a bioartificial extracellular matrix supporting cells or tissue. According to some applications, biocompatible solid depots may be implanted which release active ingredients such as proteins and drugs over time.

The delayed self gelling alginate is particularly useful as a tissue bulking material in that it can be introduced to a site that is remotely accessible and dispensed as a liquid slurry to more fully conform to a cavity relative to other types of implants. The dispersion can be dispensed in an amount sufficient to displace and support other tissues or organs in the body and upon formation of a gel in situ provide structure to maintain and support the other tissue or organs. The delayed self gelling alginate may comprise components that make it well suited for tissue bulking applications. For example, the use of strontium as a gelling agent will result in a gel that inhibits cell overgrowth and unwanted tissue formation. The delayed self gelling alginate may be handled for sufficient time to allow for implantation without gelling in catheters and the like.

The delayed self gelling alginate is particularly well suited for cardiac application in which it is particularly undesirable to have to use and position multiple catheters due to gelling in the catheter. The delayed self gelling gives the user time to properly position and deliver the dispersion.

The delayed self gelling alginate is particularly useful in embolization procedures in that it can be introduced to a blood vessel that is remotely accessible and dispensed as a liquid slurry to fully conform to interior or the blood vessel and more fully and effectively block it off relative to other types of closures such as sutures. The dispersion can be dispensed in an amount sufficient to block off circulation upon formation of a gel in situ. The delayed self gelling alginate may comprise components that make it well suited for embolization applications. For example, the components can be selected for relatively fast setting and high strength. The delayed self gelling alginate used in embolization applications may include contrast reagents to monitor its presence and location.

The delayed self gelling alginate is particularly useful in anti-adhesion treatment as post-surgical procedures in that it can be introduced throughout the area of surgical intervention as a liquid slurry to fully cover exposed surfaces particularly at or near incision sites. The delayed self gelling alginate may comprise components that make it well suited for anti-adhesion applications. For example, the use of strontium as a gelling agent will result in a gel that inhibits cell overgrowth and unwanted tissue formation.

The delayed self gelling alginate is particularly useful wound treatment in that it can be introduced throughout the area of wound as a liquid slurry to fully cover exposed surfaces. In addition, the delayed self gelling alginate can be dispensed internally through the wound site for example as a liquid slurry. The dispersion can be dispensed in an amount sufficiently to fill the internal cavity whereupon formation of a gel in situ the gel will block off any internal wounds and prevent blood loss through internal bleeding. The delayed self gelling alginate may comprise components that make it well suited for wound treating applications. For example, blood clotting components as well as antiseptic and antibiotic compositions may be included.

The delayed self gelling alginate is particularly useful to produce tissue constructs ex vivo or in vivo. Cells or other biomaterials may be mixed into the gelling system thereby creating a bioartificial extracellular matrix supporting cells or tissue. The dispersion can be introduced in situ as a liquid slurry to a site where the tissue/cells can function to achieve a therapeutic effect. Examples of tissue constructs include bone, cartilage, connective tissue, muscle, liver, cardiac, pancreas and skin. Examples of this may be preparations containing insulin-secreting cells for the treatment of diabetes, formulations containing chondrocytes for the repair of defective joints, and cells for treating Parkinson's disease. Such cells can be incorporated into the liquid slurry and dispensed into the site where upon gel formation they will exist and function within a biocompatible alginate matrix. The gel may also be used as an immune-barrier protecting entrapped cells against the host immune system. Delayed self-gelling alginate may also be used to encapsulate cells ex vivo whereby the gel can be formed into a shape compatible with its intended use. In some embodiments, the delayed self-gelling alginate may be used to encapsulate cells, such as dermal cells, and prepare artificial skin such as that which is used to treat burn victims and others in need of skin grafts or large area wound healing. In some embodiments, the delayed self-gelling alginates may be used to encapsulate cells and form matrices which can be implanted.

The treatment of diabetes may comprise the production of a biocompatible matrix comprising insulin producing cells by preparing dispersion comprising insoluble alginate/gelling ion particles and insulin producing cells in a solution of soluble alginate and dispensing the dispersion to a site in an individual's body where the biocompatible matrix forms. The site within the individual body may be a cavity or a structure implanted within the individual. The dispersion may be dispensed into a mold, structure or container where is forms a biocompatible matrix which is implanted into the body of an individual. The insulin produced by the cells in the matrix is secreted by the cells and released from the matrix into the body of the individual where it functions to alleviate the symptoms of the diabetic condition. In some embodiments, the insulin producing cells are pancreatic islet cells. In some embodiments, the insulin producing cells are recombinant cells produced to express and secrete insulin.

The delayed self gelling alginate is particularly useful to produce coated devices such as implantable devises. In some embodiments, the device is selected from the group consisting of: a stent, a cardiac pacemaker, a catheter, an implantable prosthetic, a surgical screw, a surgical wire, a tissue bulking implant, an esophagus reflux inhibiting implant, an incontinence inhibiting implant, a renal reflux, a container suitable for holding cells that are deposited on the exterior of a surface and/or encapsulated with an alginate matrix such as a solid device or macrocapsule, a breast implant, a chin implant, a cheek implant, a pectoral implant, a gluteus implant and a dental implant. The coating using delayed self gelling alginate produces an effective coating regardless of shape. The use of strontium as gelling ion is particularly useful to inhibit cell overgrowth upon implantation.

Delayed self-gelling alginates may be used in the manufacture of matrices which can be implanted. Such matrices can be prepared with specific shapes by preparing a liquid/slurry mixture that is dispensed into a mold where it sets to form a solid with a molded shape. Matrices prepared for implantation may comprise biologically active agents and/or cell. The gels may be produced and implanted surgically, applied topically or into an organ through external openings.

According to some embodiments, kits are provided for producing an alginate gel. The kits may comprise a first container comprising soluble alginate; and a second container comprising insoluble alginate/gelling ion particles. The individual containers may be separate container compartments of an integrated container system.

In some embodiments, the kits comprise soluble alginate in the form of a solution. In some embodiments, the kits comprise soluble alginate free of a solvent. In some embodiments, the kits comprise an additional container comprising a solvent.

In some embodiments, the kits comprise insoluble alginate/gelling ion particles in the form of a powder. In some embodiments, the kits comprise insoluble alginate/gelling ion particles in the form of a dispersion.

In some embodiments, the kits comprise an additional container comprising a drug, a peptide, a protein, a cell, a detectable label or a contrast reagent. In some embodiments, the kits comprise a drug, a peptide, a protein, a cell, a detectable label or a contrast reagent included in the container comprising soluble alginate solution or powder and/or in the container comprising insoluble alginate/gelling ion powder or dispersion.

According to some embodiments, compositions are provided for preparing a gel. The composition comprises an immediately soluble alginate and insoluble alginate/gelling ion particles. The composition may further comprise a drug, a peptide, a protein, a detectable label or a contrast reagent. The composition may be a component in a kit. Such a kit may further comprise a container with a solvent.

Kits preferably contains instructions for use.

In some embodiments, the kits comprise a mixing device. Mixing devices may be integrated as part of a container or container system. In some embodiments, the mixing device comprises a valve system which allows for passage of the dispersion from one container to a different container to facilitate mixing.

In some embodiments, the kits comprise a dispensing device. The dispensing device may be an applicator in communication with a mixing device and/or a container adapted for containing the dispersion. In some embodiments, the dispensing device comprises a catheter. In some embodiments, the dispensing device comprises a syringe.

EXAMPLES

Example 1

Gelling Performance of Compositions with High G Content Calcium (CaG) Alginate Particles Four different formulations (Table 1) were made and measured under otherwise equal conditions. The setting of the gels were measured using Bohlin CVO 120 HR rheometer (measuring system used serrated plates, at 20° C., gap 1 mm, frequency 1.0 Hz, strain 0.005) immediately after mixing the components using two connected syringes (4 ml sample, mixed 20 seconds, measurements started about one minute after start mixing.) Time is zero at the start of mixing. The gelling process started almost immediately after mixing when using calcium alginate particles prepared with a high content of mannuronic acid (formulation 1 and 3 in Table 1. and Formulation 3 FIG. 1). The high M insoluble alginate particles (CaM) used alginate which contained less than about 50% guluronic acid. In contrast there was a significant initial delay time before gelling was observed when using compositions of the present inventions containing calcium alginate particles with a high content of guluronic acid (see FIG. 1: Formulation 17, 19 and 21, the insoluble high G alginate particles CaG used alginate that contained about 70% guluronic acid with long G-blocks.). The G blocks length is measured according to the reference Ø. Skaugrud, A. Hagen, B. Borgersen, and M. Dornish. Biomedical and pharmaceutical applications of alginate and chitosan. Biotechnol. Genet. Eng. Rev. 16:23-40, 1999. Formulations 1, 3 and 10 are comparative examples, and Formulations 17, 19 and 21 are examples of the present invention.

TABLE 1

Compositions

| | Component A = alginate solution (batch #) | Component B = Insoluble alginate/ gelling ion particle dispersion (batch #) | Mix ratio A:B & final alginate concentration |
|---|---|---|---|
| Formulation 1 | 1.25% SLG20 | 5% Calcium M (CaM) | 4:1/2.0% |
| Formulation 3 | 2% LVM (FP-401-06) | 2% Calcium M (CaM, FP-701-01 45-75 μm) | 1:1/2.0% |
| Formulation 10 | 2% SLM 100 | 5% Calcium M (CaM) | 1:1/3.5% |
| Formulation 17 | 2% LVM (FP-401-06) | 2% Calcium G (CaG, BP-0706-01 45-75 μm) | 1:1/2.0% |
| Formulation 19 | 3% LVM (FP-401-06) | 3% Calcium G (CaG, BP-0706-01 45-75 μm) | 1:1/3.0% |
| Formulation 21 | 2% LVG (FP-408-02) | 2% Calcium G (CaG, FP-508-03 45-75 μm) | 1:1/2.0% |

The data for the elastic modulus (G') shown in FIG. 1 was fitted a dual kinetic equation:

$$G'=A(1-f\exp(-k1(t-c))-(1-f)\exp(-k2(t-c))),$$

where A is the final gel strength, f is a relative contribution factor, k1 and k2 are rate constants, c is the delay constant (=delay time) and t is time after mixing. The total gelling half time and final gel strength was obtained from the fitted data (Table 2). The fitted equation could not be used to describe the initial part of the curve (delay) shown by the observation data for formulation 17 and 19. Calculated data from the fitted curves (final gel strength and gelling time) are shown in Table 2. The delayed self gelling time (c) is equal to time where the fitted equations reaches zero. From the data in can be seen that the Formulation 19 (CaG formulation) required about 5 minutes additional time in order to reach a similar elastic modulus (half time) as compared to the CaM formulation. The final elastic modulus was higher for this higher concentration CaG formulation. Under otherwise equal conditions of concentration, the CaG particles increased the gelling half time from about two to 20 minutes as compared to CaM particles (comparison of Formulation 3 and 17). That the gelling rate was slower for formulations containing CaG particles was confirmed by testing a delayed self gelling composition using a soluble sodium alginate with a high G content in the alginate solution (Formulation 21).

TABLE 2

Gelling parameters derived from fitted curves in FIG. 1.

| | Delay in gelling start (c) | Gelling half time ($t_{1/2}$) | Effective half time (c + $t_{1/2}$) | Final gel strength (A) |
|---|---|---|---|---|
| Formulation 1 (Comparative) | 0.7 minutes | 1.9 | 2.6 | 2.9 kPa |
| Formulation 3 (Comparative) | 0.5 minutes | 1.8 minutes | 2.3 minutes | 5.2 kPa |
| Formulation 10 (Comparative) | 0.24 minutes | 2.6 minutes | 2.8 minutes | 14.4 kPa |
| Formulation 17 (alginate = CaM) | 3.4 minutes | 20.4 minutes | 23.8 minutes | 2.1 kPa |
| Formulation 19 (alginate = CaG) | 2.0 minutes | 6.3 minutes | 8.3 minutes | 7.7 kPa |
| Formulation 21 (alginate = CaG) | 4.8 minutes | 20.7 minutes | 25.5 minutes | 2.2 kPa |

The gelling time seen for the compositions containing CaG particles holds the possibility to develop application specific formulations with improved properties. Other gelling formulations using insoluble alginate particles exhibit a delay in the onset of gelling of several hours and a delay before onset of gelling of at least one or several days. Rapid onset of gelling of the formulations may be initiated by adding sodium ions to the formulations. Gelling is initiated rapidly in the presence of physiologic levels of sodium. For example, injected delayed self-gel solutions therefore start to form a gel immediately after injection into a tissue or by adding a cell culture media which contains physiologic levels of sodium and calcium to the delayed self gelling formulation.

Insoluble alginate particles prepared using low molecular weight G block alginate are shown in Examples 2 and 3.

Example 2

Production of Calcium Alginate with Stoichiometric Amounts of Calcium (100% Saturation) and Sodium Alginate Oligomers with High Guluronic Content 75 grams of alginate oligomers (batch FP-702-01, guluronic content 73%, 4000 g/mol weight) were dissolved in 4.5 liters purified water. A calcium solution consisting of 207 grams of $CaCl_2.2H_2O$ dissolved in 450 mL of purified water was carefully added to the alginate solution under continuous stirring. A fine precipitation resulted. The precipitation was left at rest for 30-40 minutes. The precipitate was then washed with purified water until the conductivity in the suspension was less than 0.1 mS/cm. The product was finally freeze dried, milled and fractionated.

Example 3

Production of Calcium Alginate with Stoichiometric Amounts of Calcium (100% Saturation) and Sodium Alginate Oligomers with G Content>85% in Solution A calcium solution consisting of 151.8 grams of $CaCl_2.2H_2O$ and 330 mL purified water was carefully added to 1 liter of alginate oligomers in solution (G content>85%, pH 7, average DPn 16, dry matter of 5%). A fine precipitation resulted and it was left for rest overnight. The product was washed with purified water until conductivity in the suspension reached <0.1 mS/cm. The precipitated product was dried by freeze drying, crushed with a beating vat and fractionated.

Example 4

Production of Calcium Alginate with Stoichiometric Amounts of Calcium (100% Saturation) and Sodium Alginate with High Guluronic Content Suspended in an Alcohol 10 grams of PRONOVA VLVG sodium alginate, batch BP0709-02 (68% guluronic content 30 000 g/mol weight) were suspended in 420 mL isopropyl alcohol (IPA). A calcium solution consisting of 27.6 grams of $CaCl_2.2H_2O$ and 240 mL of purified water was carefully added to the solution. The suspension was left under stirring overnight before it was washed with 65% IPA. The product was dried in a drying cupboard overnight, crushed with a beating vat and fractionated.

Example 5

Production of Calcium Alginate with Stoichiometric Amounts of Calcium (100% Saturation) and Alginate with High Mannuronic Content Suspended in an Alcohol 60 grams of PRONOVA LVM (54% mannuronic content, 20 700 g/mol weight) were suspended in 2574 mL IPA. A calcium solution consisting of 165.6 grams of $CaCl_2.2H_2O$ and 1386 mL of purified water was carefully added to the solution. The suspension was left with stirring overnight. The precipitate was divided into three parts that was washed individually with water, 65% IPA and 100% IPA. The three parts were dried in a drying cupboard for ~66 hours and crushed with a beating vat.

Example 6

Further Examples of Products Produced from Different Types of Sodium Alginates with Varying DPn, G- and M Content

TABLE 3

| Batch | Alginate type | G content | M content | Average DPn |
|---|---|---|---|---|
| J96-040-02 | Alginate oligomers | 73 | 27 | 16 |
| BU-0709-01 | Alginate oligomers | 73 | 27 | 16 |
| J101#004A | Alginate oligomers | 91 | 9 | 18 |
| J101#004B | Alginate oligomers | 83 | 17 | 30 |
| J101#005 | PRONOVA VLVG | 68 | 32 | 26 |
| BU-0710-01 | Alginate oligomers | 89 | 11 | 17 |
| J101#008 | PRONOVA LVM | 46 | 54 | 26 |
| BU0711-01 | Alginate oligomers | 89 | 11 | 17 |
| BU0712-01 | Alginate oligomers | 89 | 11 | 17 |
| J101#016 | Alginate oligomers | >85 | <15 | 16 |
| J101#018 | Alginate oligomers | >85 | <15 | 16 |

In Table 3, G content refers to the percentage of G present, M content refers to the percentage of M present and average DPn corresponds to the number of monomers per oligomer.

Example 7

Delayed Self-Gels with Calcium G-Block Particles

Figure 2:
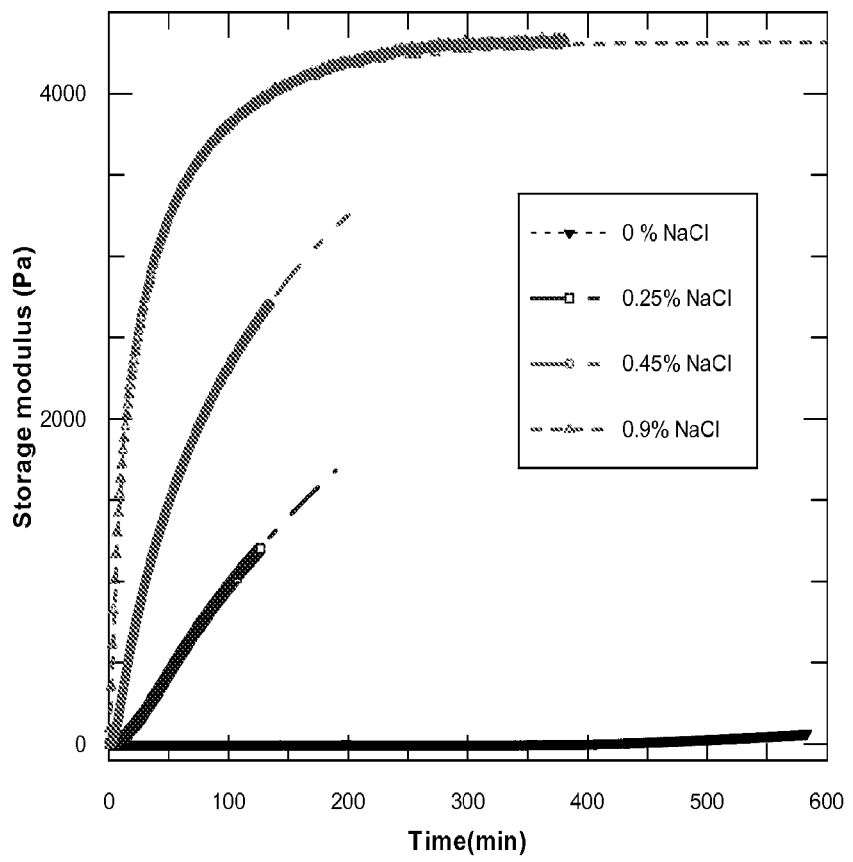
FIG. 2 shows storage modulus as a function of time for formulations made of 2.0% calcium G-block particles and 2.0% PRONOVA LVG alginate solution in the absence or presence of different NaCl concentrations.

In this example different delayed self-gel formulations were made and measured under otherwise equal conditions. As the calcium source in the gel formulations calcium G-block alginate manufactured by NovaMatrix (Batch: BU-0711-01, 45-75 µm) were used. In the formulations a 2.5% calcium G-block alginate dispersions were mixed with a solution of 2.5% PRONOVA LVG sodium alginate (Batch: FP-206-01). Three different formulations were made either without or with added sodium chloride to the sodium alginate solution so that the final sodium chloride concentration after mixing was 0.45 or 0.9%. The setting of the gels were measured using Bohlin CVO 120 HR rheometry as described in Example 1. Immediately after mixing by using two connected syringes (3 ml sample, mixed for about 20 seconds, measurements started one minute after start mixing) the formulation was placed on the rheometer. Time is zero at the start of mixing and the data is shown in FIG. 2. While the gelling process started within less than a minute in the presence of sodium chloride no gelling could be demonstrated up to about 5 hours by the rheometer data in the absence of sodium. After that only a very small change in the storage modulus could be seen indicating some degree of structure build up. However, with time (days) this formulation also resulted in a gel with final elasticity values comparable to formulations with added sodium.

Figure 3:
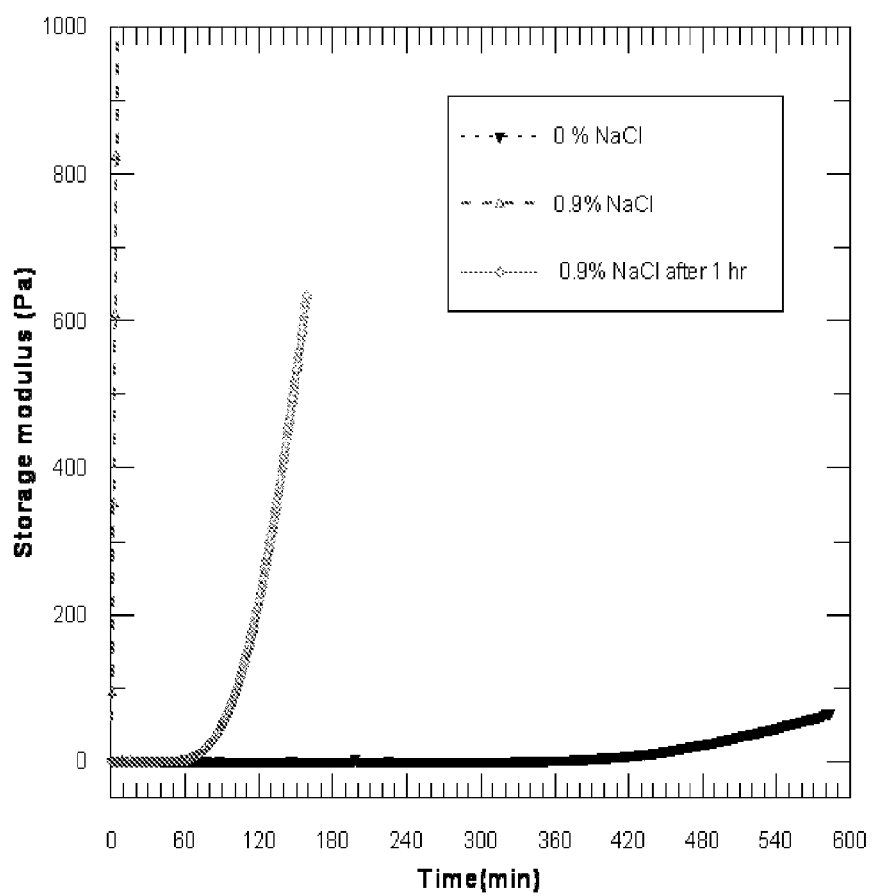
FIG. 3 shows storage modulus as a function of time for formulations made of 2.0% calcium G-block particles and 2.0% PRONOVA LVG alginate solution in the absence or presence of different 0.9 NaCl concentrations either as a part of the mixture or applied externally (placed on to of the gel) one hour after mixing.

The effect of sodium on gel formation was also tested further by adding a 0.9% sodium chloride solution on top of the gel one hour after measurements started (FIG. 3). Clearly the addition of the sodium chloride ions resulted in a rapid gelling onset and faster gel formation.

Example 8

Delayed Self-Gel Formulations with Calcium Particles Made of PRONOVA VLVG Alginate In this example different delayed self-gel formulations were made and measured under otherwise equal conditions.

Figure 4:
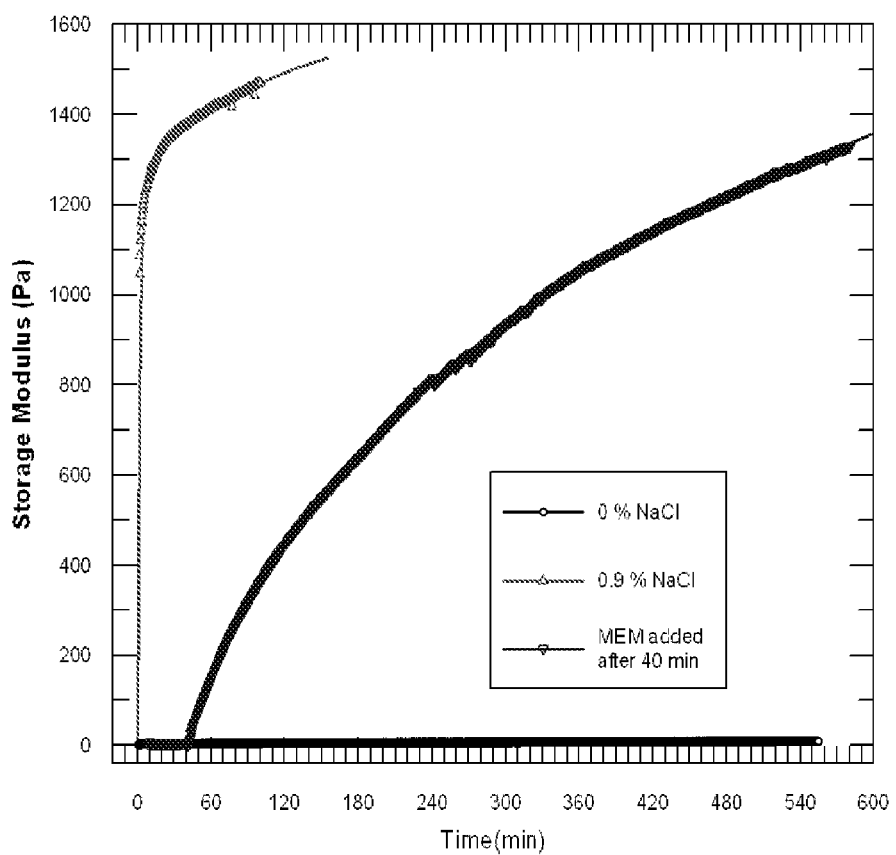
FIG. 4 shows storage modulus as a function of time for formulations made of 2.5% calcium VLVG particles (Batch: J101-005) and 2.5% PRONOVA LVG (FP-408-02) alginate solution in the absence or presence of sodium chloride. In one testing MEM cell culture medium (containing 0.9% NaCl) was applied externally (placed on top of the gel) 40 minutes after mixing.

As the calcium source in the gel formulations a specially processed calcium alginate manufactured by NovaMatrix (Batch: J101-005) were used. In the formulations a 2.5% calcium VLVG alginate dispersions were mixed with a solution of 2.5% PRONOVA LVG sodium alginate (Batch: FP-408-02). Two different formulations were made either without or with added sodium chloride to the sodium alginate solution so that the final sodium chloride concentration after mixing was 0.9%. The setting of the gels were measured using Bohlin CVO 120 HR rheometry as described in Example 1. Immediately after mixing the components using two connected syringes (3 ml sample, mixed for about 20 seconds, measurements started one minute after start mixing) were placed on the rheometer. Time is zero at the start of mixing and the data is shown in FIG. 4. While the gelling process started immediately in the presence of sodium chloride no gelling could be demonstrated by the rheometer as long as measurements were performed (more than 9 hours) in the absence of sodium. Some gelling may have occurred after one or more days. The effect of sodium on gel formation was also tested further by adding a MEM medium solution (which contains 0.9% NaCl) to the solution alginate solution one hour after measurements started (FIG. 3). Clearly the addition of the physiologic solution initiated gel formation immediately after the medium was added.

Example 9

Controlled Release Systems

The usefulness of alginate in controlled release systems for the delivery of drugs or other therapeutic molecules has been demonstrated. The type of gel preparations demonstrated here may also be used similarly and have advantages in different formulations. One example is the use of biodegradable gels, i.e. by using a low concentration of gelling ions in order to limit the treatment period. In the treatment of cancer patients a space-filling gel containing drugs or radioactive isotopes may be applied during surgical procedures in order to prevent recidive of the disease. After the active substances are released or radioactivity has decayed it may be desirable that the gel dissolves and is excreted from the body. Delayed self-gelling alginate controlled delivery formulations may of course also be injected directly into the body without any surgical procedures and the gel/alginate solution may also be used for oral drug delivery. For oral use alginate is currently well known in formulations as an anti-reflux remedy. It is therefore also possible that alginate delayed self-gelling formulations may find similar uses.

Example 10

Tissue Engineering Applications

The entrapment of cells within the alginate gel as presented here may be used to produce implantable "biofactories" excreting active substances for the treatment of a variety of diseases. However, the entrapment of cells within the alginate gel may also be used in tissue engineering applications. For tissue engineering the growth of cells within or on 3-dimensional constructs is needed and therefore good biomaterials for such applications are needed. The time-delayed self release of cross-linking ions allows the gelling-ion alginate suspension to be molded into complex geometries before gelation occurs. Under ex vivo conditions such alginate structures may be used as a growth substrate in the development of tissue or artificial organs. Cells grow on the surface of alginate gel beads as the gel surface may be a growth substrate for cells. The growth of cells on alginate gels have been found to be dependent of the alginate and the gelling ions used. The present delayed self-gelling formulation may be used to create multiple layers of cells growing inside or on the surface of alginate sheets or other shaped gel structures. Furthermore, the alginate gel may later be removed through treatment with citrate, phosphates or other gelling ion chelating agents. This gives the possibility to combine several cell layers in the construction of tissues or organs. Several types of cells inside or on the surface of gel structures may be combined if this is desirable for the development of the construct.

Nerve regeneration is an interesting example of the use of alginate within tissue engineering. The filling of artificial nerve conduits with delayed self-gelling alginate may be suitable for the creation of constructs with improved guidance and biocompatibility for nerve regrowth. This system may give better flexibility and better control over molding processes and structure properties as compared to other techniques.

Injectable alginate/cell suspension systems may also be delivered to the defective or damaged tissue site even without surgical intervention. For such applications it may be critical to have a certain working time to shape the material before it gels. However, the gelation rate may also be required to be reasonable rapid so that a prolonged patient waiting time or problems with applying the gel/solution can be avoided. The delayed self-gelling system may as shown here and previously mentioned be adapted with different gelling time-curves and different strength and stability properties. This variability may therefore be used to adapt to each type of injection procedures. As an example the repair of cartilage defects holds a potential for the use delayed self-gelling alginate structures. Alginate has been found to be a useful biomaterial to be used for cartilage tissue engineering, and it has been found that alginate may stimulate chondrogenesis. Therefore delayed self-gelling alginate solutions with or without chondrocytes or other cells may be directly injected in the treatment of articular defects. Osteoarthritis patients are already today being treated with "joint fluid therapy" and there are two products on the market, sodium hyaluronate (Hyalgan) and hylan G-F 20 (Synvisc) which are believed to work as lubricants by supplementing hyaluronic acid, the substance that gives joint fluid its viscosity. Pain relief lasts as long as six to 13 months in some people. The therapies have proven most effective for people with mild to moderate knee osteoarthritis. However, as hyaluronic acid is known to be degraded in the body the use of other biopolymers like alginate with less biodegradability and good biocompatibility provide advantages.

Alginate hydrogels may be lyophilized or the water be removed partly or fully in other ways treated in order to create biocompatible structures like sponges or fibers. The use of the technology presented here, using delayed self-gelling alginate systems, may also be used as a step in the manufacturing of biocompatible sponges or other structures which are useful for tissue engineering or other applications.

Delayed self gelling alginate formulations may be used in the coating of stents or grafts or other implantation devices. Depending of the type of alginate formulation the coating layer may be made more or less biodegradable and give more or less support for the ingrowth of host cells or the growth of cells added to the device.

Example 11

Tissue Bulking

Alginate may be delivered into the submucosa proximal to the urethral sphincter to provide bulking for the treatment of bladder incontinence and procedures has already been performed in the clinic. Another example may be the delivery of alginate formulations at the junction between the esophagus and the stomach to aid in the treatment of gastro-esophageal reflux disorders. The high degree of compatibility of alginates makes the use as an injectable solution in cosmetic procedures an attractive alternative to other materials.

Formulations based upon delayed self-gelling alginate systems may be used to create injectable solutions or pastes with predefined hardening time with purpose of filling a predefined volume. As previously mentioned gel formulations may be made more or less biodegradable giving the bulking formulation a desirable property.

Example 12

Embolization of Blood Vessels

Methods for forming endovascular occlusions may be used to treat conditions such as arteriovenous malformations, aneurysms, excessive blood supplied to tumors, control of massive vascular hemorrhaging, and other conditions which require an embolization to alleviate the condition. Some embolic systems include the use of polymers solutions which begin to solidify or precipitate when contacted with blood or other bodily fluids. Such systems, however, suffer from the problem of the polymer solution migrating into undesired parts of the body because of the time delay necessary to cause formation or precipitation of the solid polymer. Migration in these polymer solution systems is particularly problematic when the solution is injected into "high flow" areas, such as vascular systems. Fibers formed from polymer solution systems also tend to suffer from other problems, such as not embolizing well, being overly brittle, or not being biocompatible. The use of particles or beads of PVA (Poly vinyl alcohol) or gelatin beads have been found useful for embolization and are currently used in clinics.

Alginate based formulations have also been proposed for use in embolization procedures. It has been suggested that endovascular occlusions may be induced using calcium alginate by controlling the injections of an alginate liquid and a calcium chloride solution to meet and polymerize at a site within the vascular system targeted for occlusion. Compared to such systems, the use of delayed self-gelling alginate formulations as presented here has advantages. Treatment may be performed as single injections and the strength of the delayed self-hardening formulation may be adjusted with better control of the system. In particular delayed self-gelling alginate formulations are useful when the time before gelling and biodegradability needs to be controlled.

Example 13

Anti-Adhesion Formulations

Formation of adhesions is attributable to surgical operations, trauma, infections etc. Adhesions frequently occur after abdominal operations and represent a major clinical problem resulting in intestinal obstruction, infertility, and pain. Efforts to prevent or reduce adhesions have largely been unsuccessful; however, recently developed mechanical barriers using different biopolymers have demonstrated clinical progress in adhesion prevention.

Alginate based formulations have also been proposed as anti adhesion barriers. Anti-adhesion barriers may be formulated by using the delayed self-gelling alginate system presented here. The solution/gel formulation is premixed immediately before use and made with suitable biodegradability. Such types of formulations may also include other polymers, drugs or other supportive compounds. Additional polymers may be used to improve the properties of the gel, among others to increase the adhesion between gel structure and tissue.

Example 14

Wound Healing Formulations

Alginate dressings are commonly used to treat exuding wounds. Current alginate products for wound healing are composed of soft, non-woven fibers or pads. Alginates can absorb many times their own weight and form a gel within the wound to fill in dead space and maintain a moist environment. It has also been suggested that alginates may influence the wound healing process through more unknown mechanisms, and it has been postulated that calcium present within alginate wound dressing may influence the would healing process through influence on certain cells.

Delayed self-gelling alginate structures are capable of conforming to the three dimensional structure of a tissue surface during healing processes. Among other formulations with a more controllable and defined calcium content may be achievable as well as structures with high degree of resorbability.

Example 15

Cardiac Tissue Bulking Formulations

Delayed self gelling alginate systems are useful in tissue bulking procedures performed by introducing delayed self gel dispersion into cardiac space to improve blood flow and efficiency. In some individuals, such as those suffering from heart disease or loss of cardiac tissue due to ischemia related to myocardial infarction, blood flow and efficiency of the compromised heart may be improved by introducing delayed self gel dispersion which gels in situ. A catheter is placed in the individual's body where, one end of the catheter includes a needle or other puncturing device to pierce the heart from its interior. Delayed self gel alginate is then delivered and the presence of physiologic sodium or the introduction of additional sodium accelerates the delayed self gelling so that a gel forms in the heart. The delayed self gelling properties of delayed self gelling technology allows for the time to properly place and position the catheter and deliver the dispersion with a degree of control prior to gelation resulting in clogging the catheter and requiring the need for further catheterization. The delayed self gelling properties provide significant advantages by imparting a degree of control and a time frame to allow for less time critical action.

The invention claimed is:

1. A dispersion comprising insoluble alginate/gelling ion particles in an aqueous solution that comprises soluble alginate, wherein:
   a) the insoluble alginate/gelling ion particles comprise isolated G block oligomers having greater than 85% G and an average number of monomers of between 15-20 monomers per oligomer, wherein the dispersion exhibits less than 10% of final gel storage modulus after one minute in the absence of addition of non-gelling cations, or
   b) the insoluble alginate/gelling ion particles comprise insoluble alginate produced by the method comprising the steps:

i) suspending sodium alginate in a solvent other than water and combining said suspension with a gelling ion comprising at least one of calcium, strontium, barium, copper, nickel, zinc, lead, iron, manganese or cobalt to form a precipitate of alginate-gelling ion complexes, ii) collecting the precipitate, iii) washing out sodium or other ions that were present in the alginate, iv) drying the precipitate to remove the solvent, and v) making particles from the dried precipitate, wherein the dispersion in part b) exhibits less than 10% of final gel storage modulus after ten minutes in the absence of addition of non-gelling cations.

2. The dispersion in part a) of claim 1 wherein the dispersion exhibits less than 10% of final gel storage modulus after five minutes in the absence of addition of non-gelling cations.

3. The dispersion in parts a) and b) of claim 1 wherein the dispersion exhibits less than 10% of final gel storage modulus after twenty minutes in the absence of addition of non-gelling cations.

4. The dispersion in parts a) and b) of claim 1 wherein the dispersion exhibits less than 10% of final gel storage modulus after forty five minutes in the absence of addition of non-gelling cations.

5. The dispersion in parts a) and b) of claim 1 wherein the dispersion exhibits less than 10% of final gel storage modulus after more than sixty minutes in the absence of addition of non-gelling cations.

6. The dispersion in parts a) and b) of claim 1 wherein the dispersion exhibits more than 10% of final gel storage modulus within five hours upon addition of non-gelling cations.

7. The dispersion in parts a) and b) of claim 1 wherein the dispersion exhibits more than 25% of final gel storage modulus within five hours upon addition of non-gelling cations.

8. The dispersion in parts a) and b) of claim 1 wherein the dispersion exhibits more than 50% of final gel storage modulus within five hours upon addition of non-gelling cations.

9. The dispersion in parts a) and b) of claim 1 wherein the dispersion exhibits more than 75% of final gel storage modulus within five hours upon addition of non-gelling cations.

10. The dispersion in parts a) and b) of claim 1 wherein the dispersion exhibits more than 90% of final gel storage modulus within five hours upon addition of non-gelling cations.

11. The dispersion in parts a) and b) of claim 1 wherein the dispersion exhibits more than 10% of final gel storage modulus within one hour upon addition of non-gelling cations.

12. The dispersion in parts a) and b) of claim 1 wherein the dispersion exhibits more than 25% of final gel storage modulus within one hour upon addition of non-gelling cations.

13. The dispersion in parts a) and b) of claim 1 wherein the dispersion exhibits more than 50% of final gel storage modulus within one hour upon addition of non-gelling cations.

14. The dispersion in parts a) and b) of claim 1 wherein the dispersion exhibits more than 75% of final gel storage modulus within one hour upon addition of non-gelling cations.

15. The dispersion in parts a) and b) of claim 1 wherein the dispersion exhibits more than 90% of final gel storage modulus within one hour upon addition of non-gelling cations.

16. The dispersion in parts a) and b) of claim 1 wherein the dispersion exhibits more than 10% of final gel storage modulus within ten minutes upon addition of non-gelling cations.

17. The dispersion in parts a) and b) of claim 1 wherein the dispersion exhibits more than 25% of final gel storage modulus within ten minutes upon addition of non-gelling cations.

18. The dispersion in parts a) and b) of claim 1 wherein the dispersion exhibits more than 50% of final gel storage modulus within ten minutes upon addition of non-gelling cations.

19. The dispersion in parts a) and b) of claim 1 wherein the dispersion exhibits more than 75% of final gel storage modulus within ten minutes upon addition of non-gelling cations.

20. The dispersion in parts a) and b) of claim 1 wherein the dispersion exhibits more than 90% of final gel storage modulus within ten minutes upon addition of non-gelling cations.

21. The dispersion of claim 6 wherein the addition of non-gelling cations is sufficient to raise a final concentration of non-gelling cations by 17 mM or more, or sufficient to achieve a final concentration of about 0.9%.

22. The dispersion of claim 1 wherein the insoluble alginate/gelling ion particle comprises isolated G block oligomers having greater than 85% G and an average number of monomers of between 15-20 monomers per oligomer.

23. The dispersion of claim 1 wherein the insoluble alginate/gelling ion particle is produced by the method of part b).

24. The dispersion of claim 23 wherein the solvent other than water in part b) comprises an alcohol.

25. The dispersion of claim 1 wherein the insoluble alginate/gelling ion particle comprises calcium.

26. The dispersion of claim 1 wherein the insoluble alginate/gelling ion particles are less than 175 microns.

27. A composition for making a dispersion of claim 1 comprising immediately soluble alginate and said insoluble alginate/gelling ion particles.

28. A method for preparing an alginate gel comprising:
forming the dispersion of claim 1 by a) mixing i) a solution comprising the soluble alginate with the insoluble alginate/gelling ion particles or ii) immediately soluble alginate, insoluble alginate/gelling ion particles and a solvent;

b) combining the dispersion with or exposing the dispersion to a non-gelling cation.

29. A method for preparing an alginate gel in an individual in situ comprising:
forming the dispersion of claim 1 by a) mixing i) a solution comprising the soluble alginate with the insoluble alginate/gelling ion particles, or ii) immediately soluble alginate, insoluble alginate/gelling ion particles and a solvent;

b) dispensing the dispersion to a site in the individual's body, wherein an alginate forms at the site.

30. A method for preparing an alginate gel comprising:
a) forming the dispersion of claim 1 comprising insoluble alginate/gelling ion particles in an aqueous solution that comprises the soluble alginate by mixing i) a solution comprising the soluble alginate with the insoluble alginate/gelling ion particles or ii) immediately soluble alginate, insoluble alginate/gelling ion particles and a solvent;

b) adding to the dispersion an amount of non-gelling cation in an amount sufficient that the dispersion exhibits more than 10% of final gel storage modulus within five hours upon addition of non-gelling cations.

31. The method of claim 30 wherein the amount of non-gelling cation added to the dispersion is sufficient that the dispersion exhibits more than 10% of final gel storage modulus within one hour upon addition of non-gelling cations.

32. The method of claim 30 wherein the amount of non-gelling cation added to the dispersion is sufficient that the dispersion exhibits more than 10% of final gel storage modulus within thirty minutes upon addition of non-gelling cations.

33. The method of claim 30 wherein the amount of non-gelling cation added to the dispersion is sufficient that the dispersion exhibits more than 10% of final gel storage modulus within ten minutes upon addition of non-gelling cations.

34. The method of claim 30 wherein the amount of non-gelling cation added to the dispersion is sufficient that the dispersion exhibits more than 50% of final gel storage modulus within one hour upon addition of non-gelling cations.

35. The method of claim 30 wherein the amount of non-gelling cation added to the dispersion is sufficient that the dispersion exhibits more than 50% of final gel storage modulus within thirty minutes upon addition of non-gelling cations.

36. The method of claim 30 wherein the amount of non-gelling cation added to the dispersion is sufficient that the dispersion exhibits more than 50% of final gel storage modulus within ten minutes upon addition of non-gelling cations.

37. The method of claim 30 wherein the amount of non-gelling cation added to the dispersion is sufficient that the dispersion exhibits more than 90% of final gel storage modulus within one hour upon addition of non-gelling cations.

38. The method of claim 30 wherein the amount of non-gelling cation added to the dispersion is sufficient that the dispersion exhibits more than 90% of final gel storage modulus within thirty minutes upon addition of non-gelling cations.

39. The method of claim 30 wherein the amount of non-gelling cation added to the dispersion is sufficient that the dispersion exhibits more than 90% of final gel storage modulus within ten minutes upon addition of non-gelling cations.

40. The dispersion of claim 1, wherein said gelling ion in part b) comprises calcium and said solvent in part b) comprises alcohol.

* * * * *